United States Patent
Sako et al.

(10) Patent No.: US 9,867,595 B2
(45) Date of Patent: Jan. 16, 2018

(54) ULTRASONOGRAPHY APPARATUS AND ULTRASONOGRAPHY METHOD

(71) Applicant: SONY CORPORATION, Tokyo (JP)

(72) Inventors: Yoichiro Sako, Tokyo (JP); Kouichirou Ono, Tokyo (JP)

(73) Assignee: SONY CORPORATION, Tokyo (JP)

( * ) Notice: Subject to any disclaimer, the term of this patent is extended or adjusted under 35 U.S.C. 154(b) by 87 days.

(21) Appl. No.: 14/370,090

(22) PCT Filed: Feb. 13, 2013

(86) PCT No.: PCT/JP2013/000767
§ 371 (c)(1),
(2) Date: Jul. 1, 2014

(87) PCT Pub. No.: WO2013/125178
PCT Pub. Date: Aug. 29, 2013

(65) Prior Publication Data
US 2014/0343419 A1 Nov. 20, 2014

(30) Foreign Application Priority Data

Feb. 24, 2012 (JP) ................................. 2012-038274

(51) Int. Cl.
*A61B 8/08* (2006.01)
*A61B 8/13* (2006.01)
*A61B 8/00* (2006.01)

(52) U.S. Cl.
CPC ............. *A61B 8/5292* (2013.01); *A61B 8/13* (2013.01); *A61B 8/4245* (2013.01); *A61B 8/4254* (2013.01); *A61B 8/56* (2013.01); *A61B 8/585* (2013.01); *A61B 8/461* (2013.01); *A61B 8/5269* (2013.01); *A61B 8/54* (2013.01)

(58) Field of Classification Search
CPC ....... A61B 8/13; A61B 8/4245; A61B 8/4254; A61B 8/461; A61B 8/5269
See application file for complete search history.

(56) References Cited

U.S. PATENT DOCUMENTS 6,322,507 B1 * 11/2001 Passi .................... A61B 8/0875
600/437
2005/0240103 A1 10/2005 Byrd et al.
2008/0269610 A1 * 10/2008 Burla ....................... A61B 8/00
600/447

(Continued)

FOREIGN PATENT DOCUMENTS

JP        9-281093 A      10/1997
WO        WO 00/24307 A2   5/2000

OTHER PUBLICATIONS

International Search Report dated May 2, 2013 in Patent Application No. PCT/JP2013/000767.

*Primary Examiner* — Baisakhi Roy
(74) *Attorney, Agent, or Firm* — Chip Law Group

(57) ABSTRACT

An ultrasonographic system includes an electronic memory to store a table that relates subject information to a plurality of frequencies, and a frequency setting unit that sets the examination frequency to one of the frequencies stored in the table. The frequency setting unit sets the examination frequency based on selection of subject information from the table, and the examination frequency is used to perform ultrasound examination on the subject according to the selected information.

20 Claims, 11 Drawing Sheets

(56) References Cited

U.S. PATENT DOCUMENTS

| | | | |
|---|---|---|---|
| 2009/0326569 A1* | 12/2009 | Tanaka | A61B 17/320068 606/169 |
| 2010/0113983 A1* | 5/2010 | Heckerman | A61B 17/22004 601/2 |
| 2012/0130287 A1* | 5/2012 | Gruber | A61N 7/00 601/2 |
| 2015/0080748 A1* | 3/2015 | Hubbert | A61B 5/7282 600/481 |

* cited by examiner

[Fig. 1]

|  | ABDOMEN | ... |
|---|---|---|
| CHILD | 4 [MHz] | ... |
| ADULT | 6 [MHz] | ... |

[Fig. 2]
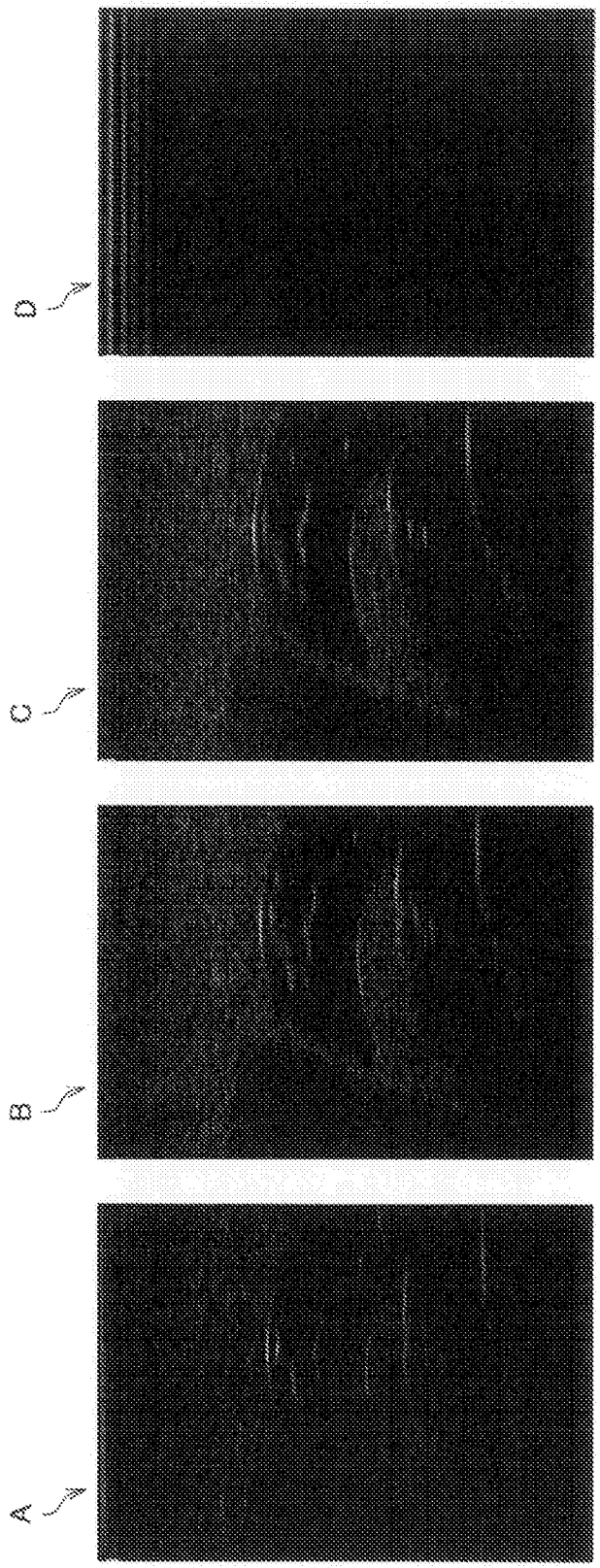

[Fig. 3]
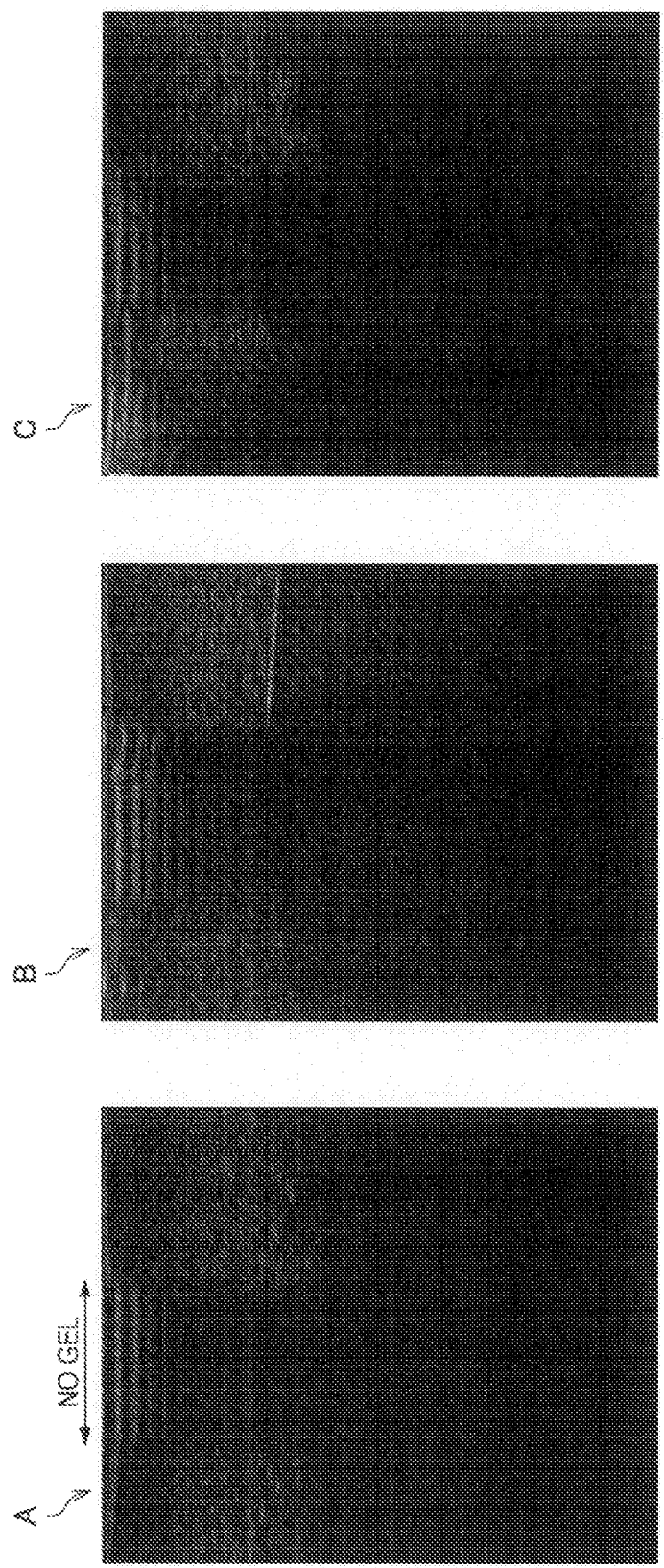

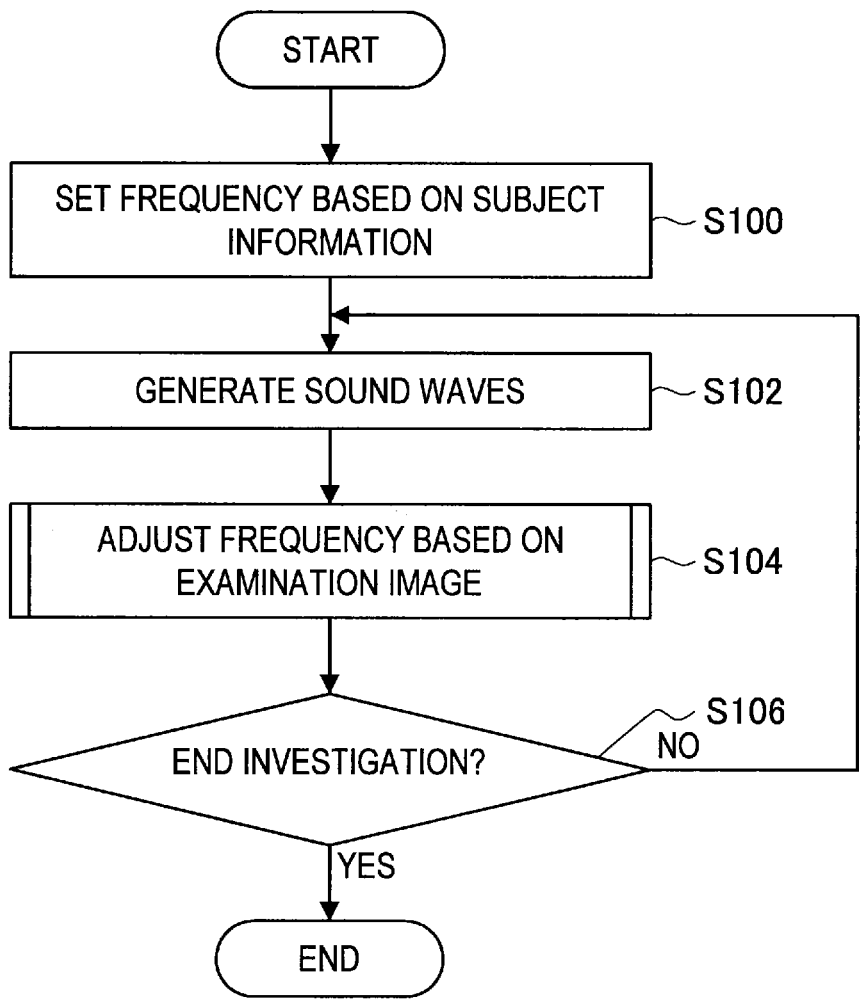
[Fig. 4]

[Fig. 5]
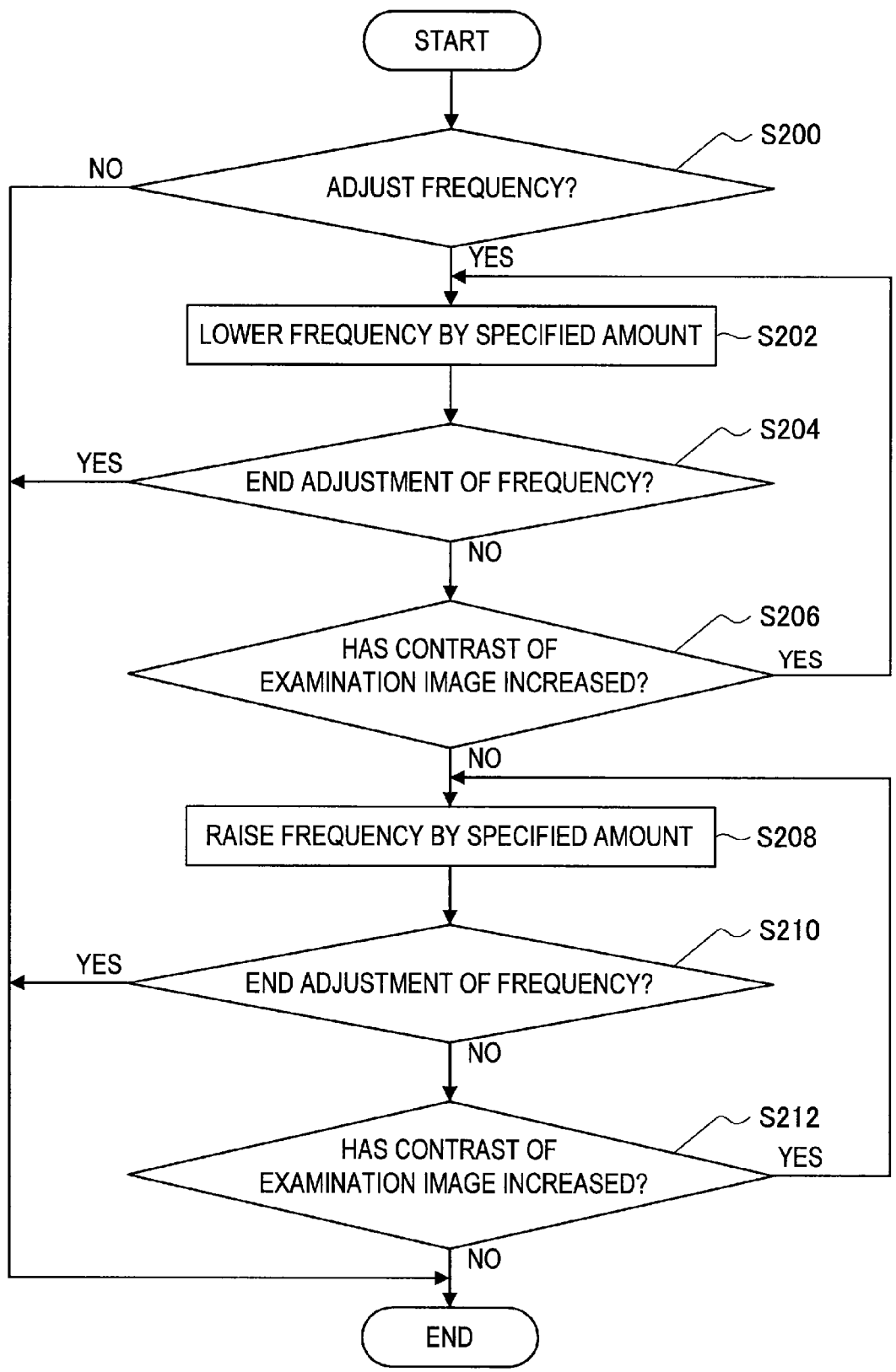

[Fig. 6]
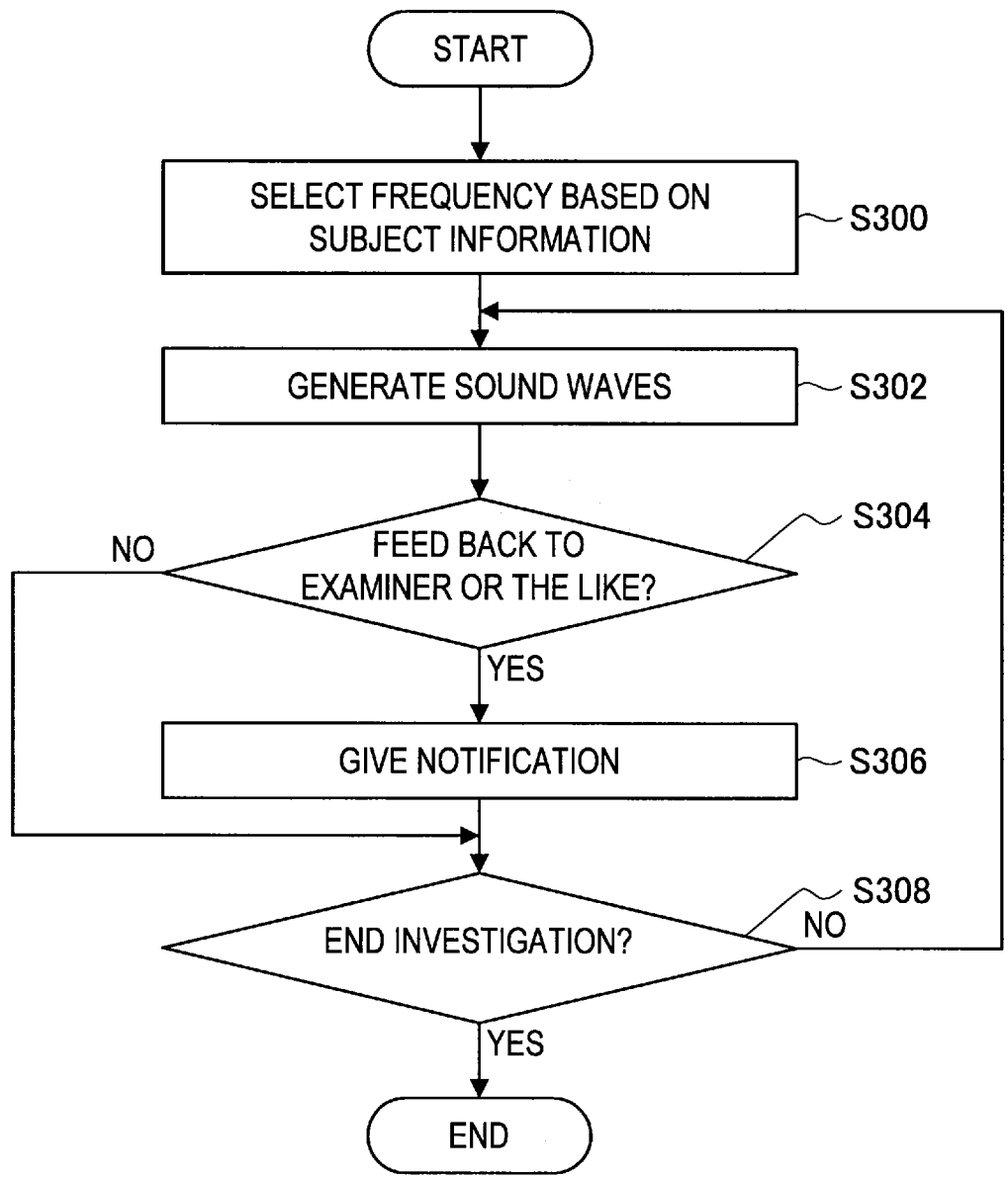

[Fig. 7]
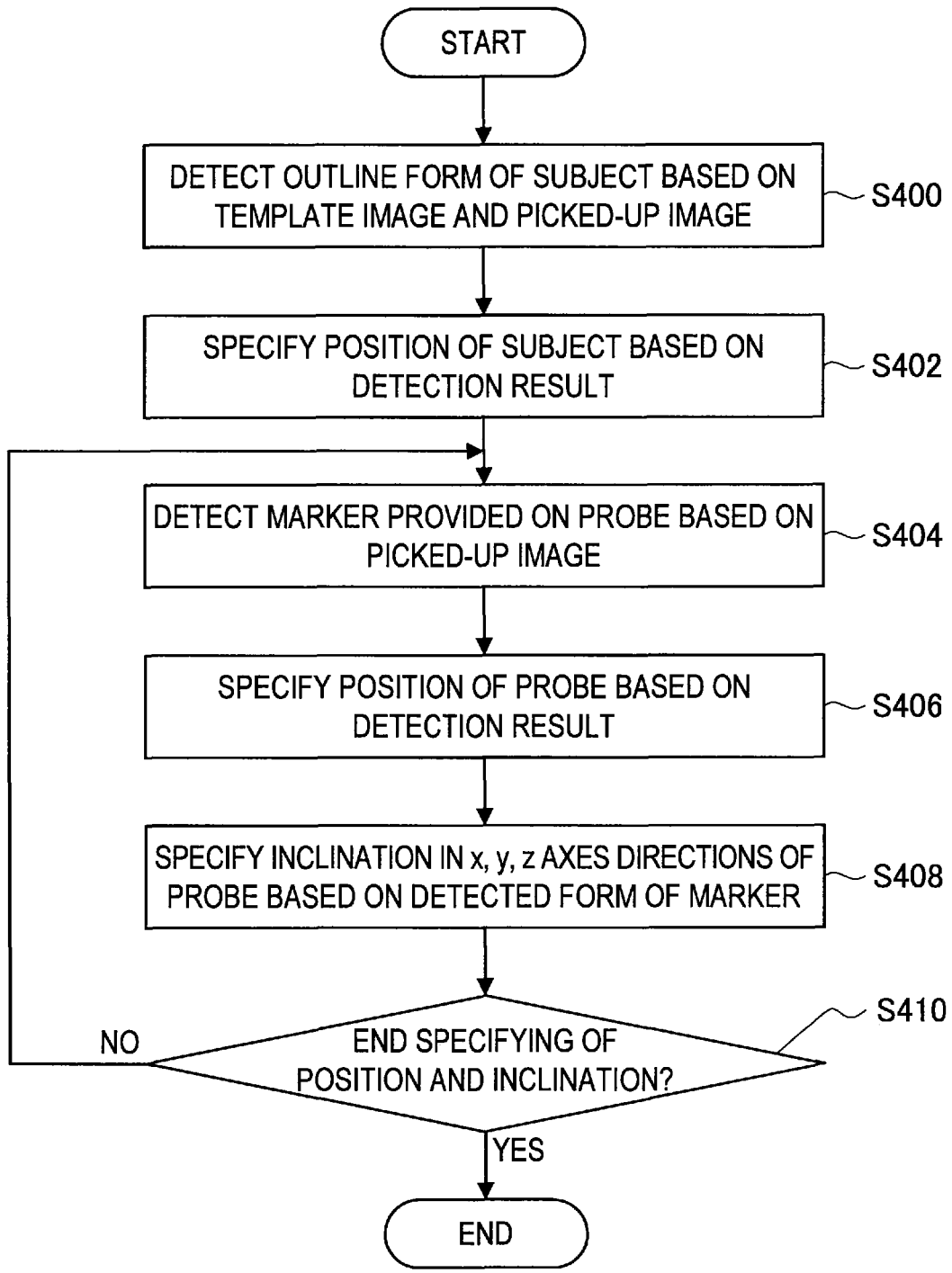

[Fig. 8]
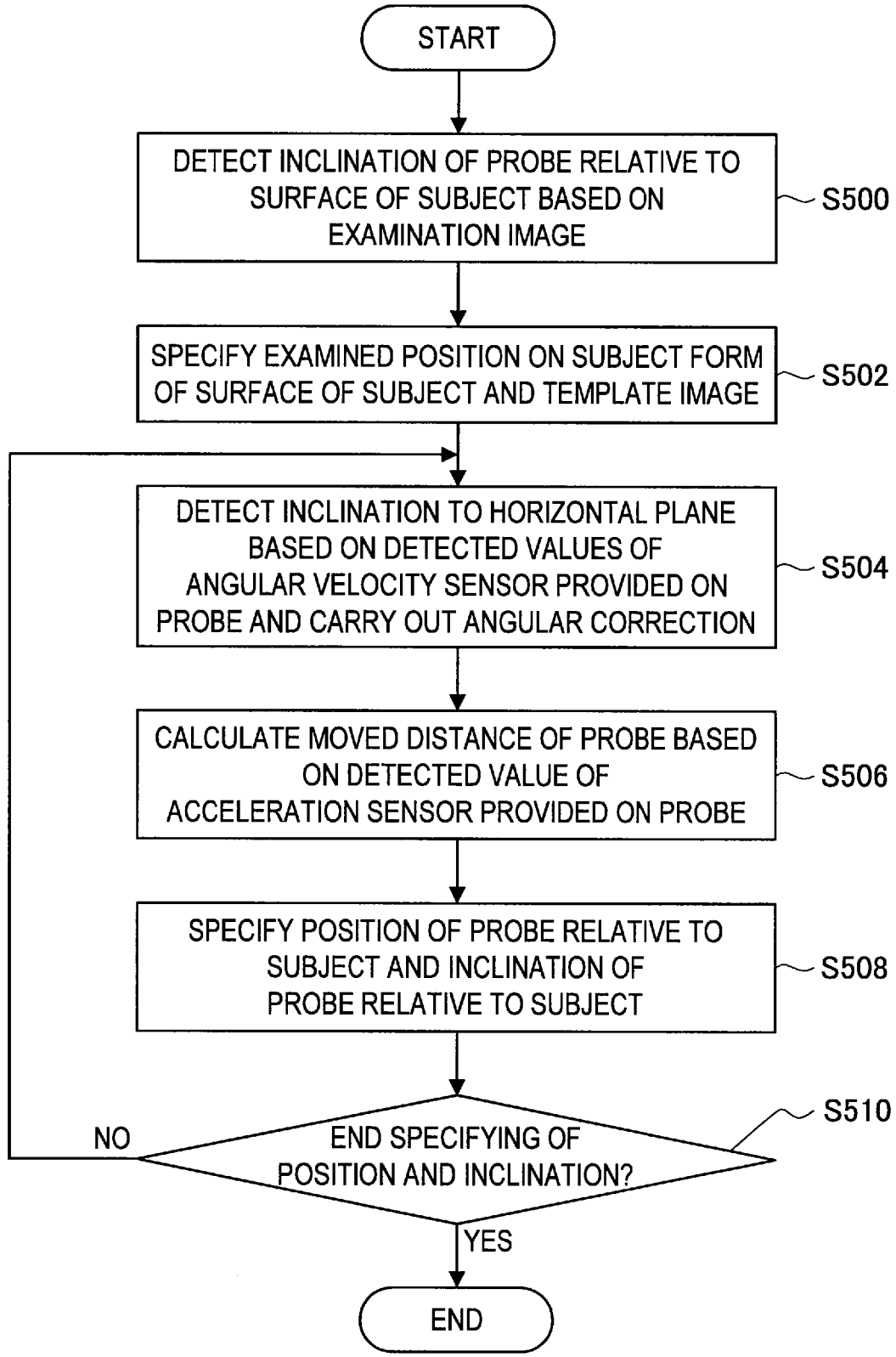

[Fig. 9]
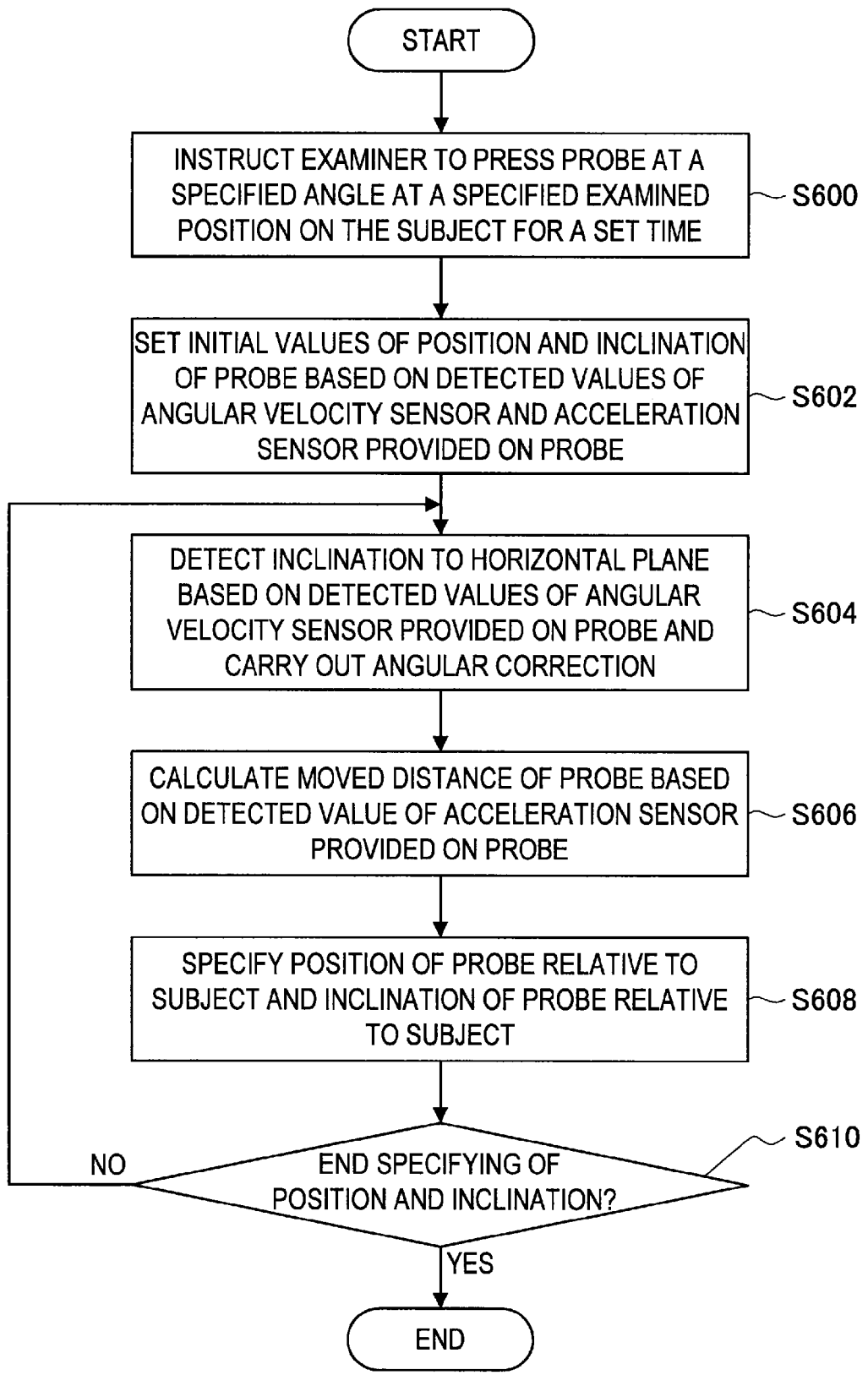

[Fig. 10]
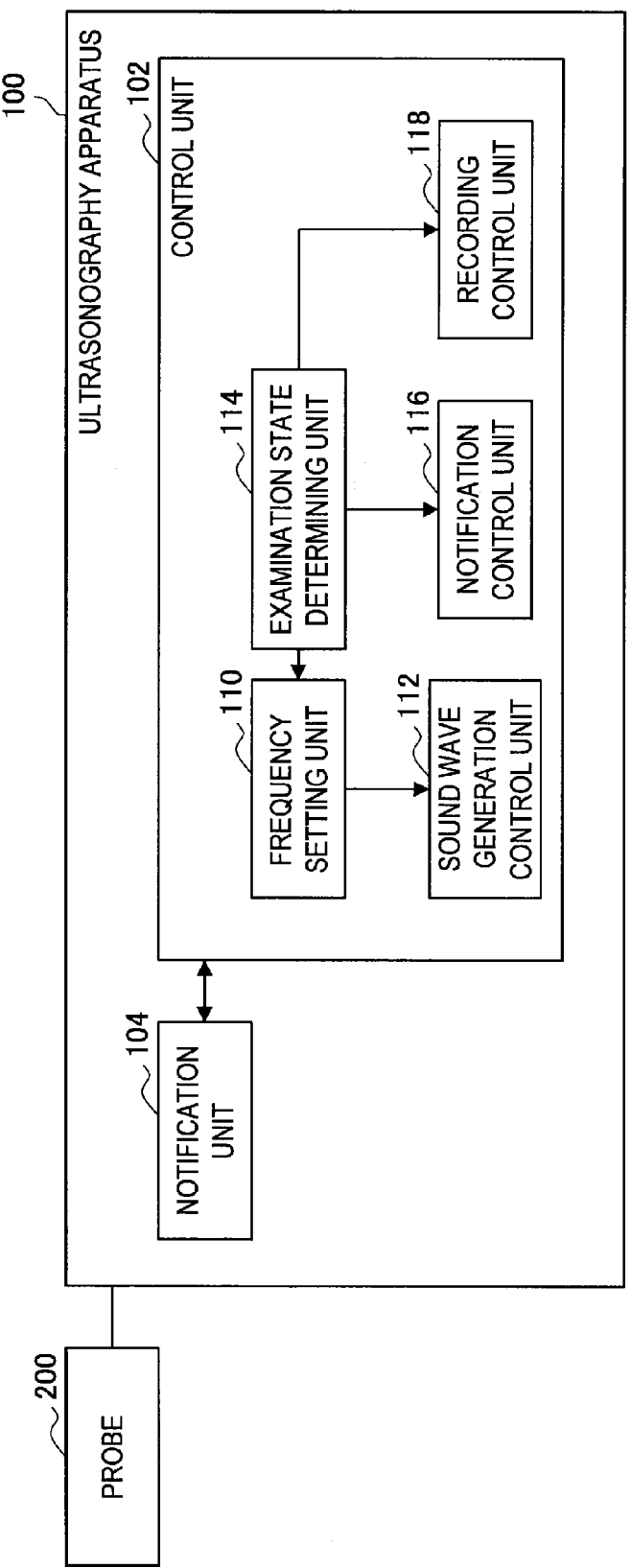

[Fig. 11]
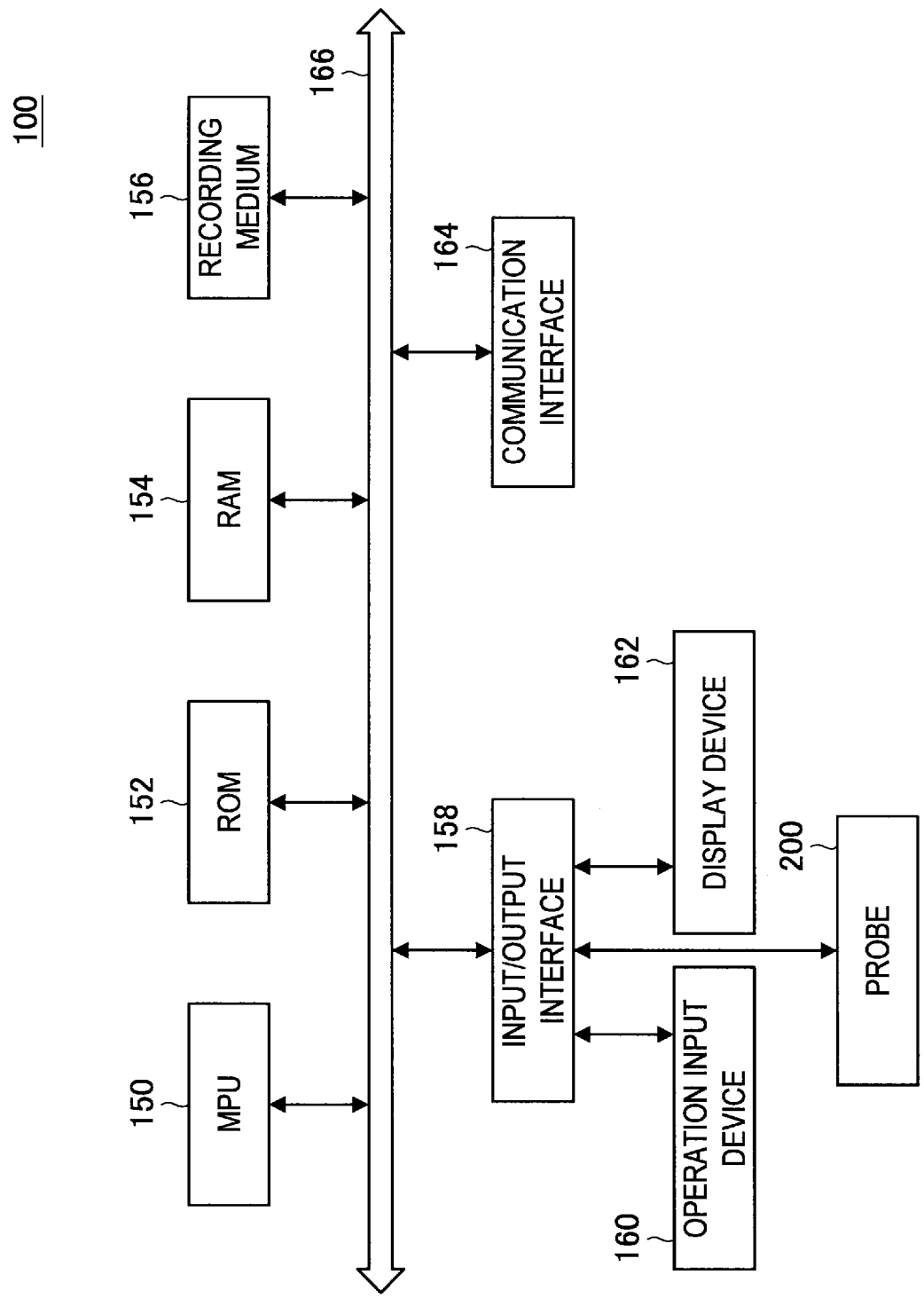

ULTRASONOGRAPHY APPARATUS AND ULTRASONOGRAPHY METHOD

TECHNICAL FIELD

The present disclosure relates to an ultrasonography apparatus, an ultrasonography method, and a program.

BACKGROUND ART

An examination method called "ultrasonography" where a subject is exposed to ultrasound, echoes produced from the subject are visualized, and an examination is carried out based on the obtained images is widely used in the field of medicine, for example. Technologies relating to ultrasonography apparatuses, i.e., apparatuses for carrying out ultrasonography, have also been developed. One example of a technology relating to ultrasonography apparatuses is disclosed in JP H09-281093A, described below.

CITATION LIST

Patent Literature

PTL 1: JP H09-281093A

SUMMARY

Technical Problem

Various individual differences, such as sex, race, and physique, exist between patients (hereinafter "subjects") subjected to ultrasonography. For this reason, if ultrasonography is carried out on a plurality of subjects using sound waves (note that this expression hereinafter includes sound (i.e., so-called "ultrasound") that is normally inaudible to the human ear) of a constant frequency, there will be differences in the acquired examination images (note that this expression hereinafter refers to images showing echoes produced from the subject as a result of generated sound waves striking the subject). Accordingly, when ultrasonography is carried out on a subject, the use of sound waves of a suitable frequency for the subject is preferable so as to obtain examination images that facilitate examination by an examiner, such as a doctor or technician, and moreover to improve the precision of an ultrasonographic examination, for example.

Here, with the technology according to JP H09-281093A, for example, ultrasound of a plurality of frequencies is transmitted from a single probe and a range from a shallow part to a deep part of the subject is simultaneously visualized. Accordingly, if ultrasonography is carried out using the technology according to JP H09-281093A, for example, there is the possibility that some of the emitted sound waves will be of a suitable frequency for the subject.

However, the technology according to JP H09-281093A, for example, does not particularly consider how to use sound waves of a suitable frequency for the subject. Accordingly, even if the technology according to JP H09-281093A is used, for example, there is no guarantee that the examiner will be able to carry out ultrasonography using sound waves of a suitable frequency for the subject.

The present disclosure aims to provide a novel and improved ultrasonography apparatus, ultrasonography method, and program that enable an examiner to carry out ultrasonography using sound waves of a suitable frequency for the subject.

Solution to Problem

An ultrasonographic system includes an electronic memory that stores a table that relates subject information to a plurality of frequencies; and a frequency setting unit to set, as an examination frequency, one of the plurality of frequencies based on selection of subject information from the table, the examination frequency being used to perform an ultrasound examination on a subject corresponding to the selected subject information.

An ultrasonographic imaging method includes storing a table relating subject information to a plurality of frequencies in an electronic memory, and setting, as an examination frequency, one of the plurality one of the plurality of frequencies based on selection of subject information from the table. The examination frequency is then used to perform an ultrasound examination on a subject corresponding to the selected subject information.

A non-transitory computer-readable medium storing computer-readable instructions thereon, where the computer-readable instructions when executed by a computer cause the computer to perform an ultrasonographic imaging method, and the method includes storing a table relating subject information to a plurality of frequencies. The method also includes setting, as an examination frequency, one of the plurality one of the plurality of frequencies based on selection of subject information from the table. The examination frequency being used to perform an ultrasound examination on a subject corresponding to the selected subject information.

Advantageous Effects of Invention

According to the above embodiments of the present disclosure, it is possible to enable an examiner to carry out an ultrasonographic examination using sound waves of a suitable frequency for the subject.

BRIEF DESCRIPTION OF DRAWINGS

FIG. 1 is a diagram useful in explaining one example of conversion information according to an embodiment of the present disclosure.

FIG. 2 is diagram useful in explaining one example of examination images processed by an ultrasonography apparatus according to the present embodiment.

FIG. 3 is diagram useful in explaining one example of examination images processed by an ultrasonography apparatus according to the present embodiment.

FIG. 4 is a flowchart showing one example of processing relating to an ultrasonography method according to the present embodiment.

FIG. 5 is a flowchart showing one example of a frequency adjusting process according to the present embodiment.

FIG. 6 is a flowchart showing another example of processing relating to the ultrasonography method according to the present embodiment.

FIG. 7 is a flowchart showing a first example of processing relating to a method of specifying the position of a probe (examination position) and the inclination of the probe according to the present embodiment.

FIG. 8 is a flowchart showing a second example of processing relating to a method of specifying the position of a probe (examination position) and the inclination of the probe according to the present embodiment.

FIG. 9 is a flowchart showing a third example of processing relating to a method of specifying the position of a probe (examination position) and the inclination of the probe according to the present embodiment.

FIG. 10 is a block diagram showing one example of the configuration of the ultrasonography apparatus according to the present embodiment.

FIG. 11 is a diagram useful in explaining one example of the hardware configuration of the ultrasonography apparatus according to the present embodiment.

DESCRIPTION OF EMBODIMENTS

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The following description is given in the order indicated below.
1. Ultrasonography Method According to an Embodiment of the Present Disclosure
2. Ultrasonography Apparatus According to an Embodiment of the Present Disclosure
3. Program According to an Embodiment of the Present Disclosure Ultrasonography Method According to an Embodiment of the Present Disclosure Before describing the configuration of an ultrasonography apparatus according to an embodiment of the present disclosure, an ultrasonography method according to an embodiment of the present disclosure will be described first. An example where processing relating to the ultrasonography method according to the present embodiment is carried out by an ultrasonography apparatus according to the present embodiment is described below.

As described above, when ultrasonography is carried out on a subject, use of sound waves of a suitable frequency for the subject is preferable in order to improve the precision of the ultrasonographic examination, for example. For this reason, the ultrasonography apparatus according to the present embodiment sets a suitable frequency for the subject based on subject information showing the subject (a frequency setting process). The ultrasonography apparatus according to the present embodiment then causes a probe capable of generating sound waves to generate sound waves of the set frequency (a sound wave generation control process).

Here, data showing one or two or more of information classifying the subject, information showing the examined part, information showing a disease content of the subject, and information showing the condition of the subject can be given as examples of "subject information" according to the present embodiment. Here, data showing one or two or more of the sex, age (in years or a simple indication of adult/child), a degree of obesity (such as a BMI (Body Mass Index) value), nationality (or race) can be given as examples of information classifying the subject. Data showing an organ, the abdomen, or a body part such as a hand or foot can be given as examples of information showing the examined part. Data showing a disease name or the progress of a disease can be given as examples of information showing a disease content of the subject. Also, data showing meal consumption by the subject (for example, the time at which the subject last took a meal before the examination and/or the meal content) can be given as an example of information showing the condition of the subject.

(1) Frequency Setting Process

The ultrasonography apparatus according to the present embodiment specifies the subject information to be used and sets a suitable frequency for the subject based on the specified subject information.

More specifically, as one example the ultrasonography apparatus according to the present embodiment specifies the subject information to be used in the frequency setting process based on a user operation (an input operation, a selection operation, or the like) made by an examiner or the like. Note that the method by which the ultrasonography apparatus according to the present embodiment specifies the subject information to be used is not limited to the example described above. As another example, the ultrasonography apparatus according to the present embodiment may specify the subject information to be used by communicating with an external apparatus that composes another system, such as an electronic medical record system so as to acquire subject information corresponding to the subject from the external apparatus. As one example, the ultrasonography apparatus according to the present embodiment may acquire the subject information corresponding to the subject from the external apparatus mentioned above by transmitting a subject information transmission request including data indicating the subject (such as an ID of the subject) and a transmission request for subject information to the external apparatus. As another example, the ultrasonography apparatus according to the present embodiment may specify the subject information to be used by reading out subject information corresponding to the subject from subject information stored in a storage unit (described later) provided in the ultrasonography apparatus according to the present embodiment.

Once the subject information to be used has been specified, as one example the ultrasonography apparatus according to the present embodiment may use the specified subject information and conversion information, such as a table in which subject information and frequencies are associated, to set a frequency that corresponds to the specified subject information.

Figure 1:
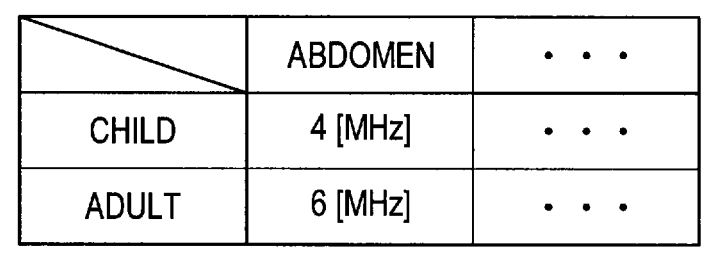

FIG. 1 is a diagram useful in explaining one example of conversion information according to the present embodiment and shows one example of a table in which information classifying the subject (adult/child shown in FIG. 1) and examined parts such as the abdomen are associated. Note that it should be obvious that the conversion information according to the present embodiment is not limited to the example shown in FIG. 1.

For example, if the specified subject information indicates "adult" and "abdomen", by using conversion information such as that shown in FIG. 1, the ultrasonography apparatus according to the present embodiment is capable of specifying a frequency of 6 (MHz). Note that the ultrasonography apparatus according to the present embodiment may specify conversion information corresponding to the specified subject information out of a plurality of conversion information based on the type of data (or combination of included data) included in the specified subject information. As examples, the ultrasonography apparatus according to the present embodiment may specify conversion information corresponding to the specified subject information by reading conversion information corresponding to the type of data included in the specified subject information from a storage unit (described later) or acquiring such conversion information from an external recording medium or an external apparatus.

As one example, the ultrasonography apparatus according to the present embodiment sets a suitable frequency for the subject by carrying out processing such as that described above.

Note that the frequency setting process by the ultrasonography apparatus according to the present embodiment is not limited to the processing described above. As one example, if a range of frequencies is set in the conversion information, the ultrasonography apparatus according to the present embodiment may specify the range of frequencies corresponding to the subject based on the subject information and shift the set frequency within the specified range of frequencies (this corresponds to a provisional setting process for the frequency). If a provisional setting process for the frequency is carried out, as one example the ultrasonography apparatus according to the present embodiment sets a suitable frequency for the subject out of the shifted frequencies based on determination results for an examination state determined based on examination images obtained from the provisionally set frequencies (this corresponds to a final setting process for the frequency).

That is, it is possible for the ultrasonography apparatus according to the present embodiment to carry out a so-called "calibration" of frequency as the frequency setting process. Note that a determination process for the examination state based on examination images according to the present embodiment will be described later.

(2) Sound Wave Generation Control Process

As one example, the ultrasonography apparatus according to the present embodiment applies a voltage corresponding to the frequency set in the processing (frequency setting process) in (1) described above to a probe as an external apparatus or a probe provided in the ultrasonography apparatus according to the present embodiment (referred to in general hereinafter as the "probe according to the present embodiment"). Due to the voltage corresponding to the set frequency being applied, the probe according to the present embodiment generates sound waves of the frequency set in the processing (frequency setting process) in (1) described above.

Here, as one example, the probe according to the present embodiment includes a sound wave generating device, a backing material, an acoustic lens, and an acoustic matching layer.

The sound wave generating device may be constructed of a piezoelectric element, a crystal oscillator, or the like, and generates sound waves in accordance with the applied voltage. The sound wave generating device also serves for example as a convertor that converts echoes (i.e., external pressure) produced from the subject to a signal (i.e., changes in voltage). The ultrasonography apparatus according to the present embodiment is capable of obtaining an examination image by receiving such signal which is transmitted from the probe.

The backing material is provided on the opposite side in the direction in which sound waves are generated by the sound wave generating device and serves so as to absorb sound waves that propagate in the opposite direction to the direction in which sound waves are generated and also suppresses vibration. The acoustic lens is constructed of silicon rubber, for example, and serves so as to focus the ultrasound generated by the sound wave generating device. The acoustic matching layer is provided between the sound wave generating device and the acoustic lens and serves so as to reduce reflection of sound waves that are generated due to the difference in acoustic impedance between the sound wave generating device and the subject.

By including the sound wave generating device, the backing material, the acoustic lens, and the acoustic matching layer for example, the probe according to the present embodiment generates sound waves of a frequency in accordance with the voltage (the signal voltage transmitted by the ultrasonography apparatus according to the present embodiment) applied by the ultrasonography apparatus according to the present embodiment. Note that the configuration of the probe according to the present embodiment is not limited to the example described above. For example, the probe according to the present embodiment may include various sensors such as a pressure sensor capable of measuring a pressure value applying to the subject during ultrasonography, an angular velocity sensor, and a triaxial acceleration sensor. The probe according to the present embodiment may have an arbitrary configuration that is capable of generating sound waves of a frequency in accordance with a voltage applied by the ultrasonography apparatus according to the present embodiment.

The ultrasonography apparatus according to the present embodiment carries out the processing (frequency setting process) in (1) described above and the processing (sound wave generation control process) in (2) described above as processing relating to the ultrasonography method according to the present embodiment. Here, the ultrasonography apparatus according to the present embodiment sets a suitable frequency for the subject in the processing (frequency setting process) in (1) described above and causes the probe to generate sound waves of the set frequency in the processing (sound wave generation control process) in (2) described above.

Accordingly, the ultrasonography apparatus according to the present embodiment is capable of enabling an examiner to carry out ultrasonography using sound waves of a suitable frequency for the subject.

Note that the processing relating to the ultrasonography method according to the present embodiment is not limited to the processing (frequency setting process) in (1) described above and the processing (sound wave generation control process) in (2) described above.

For example, the ultrasonography apparatus according to the present embodiment is also capable of carrying out processing (an examination state determining process) that determines the examination state based on the clarity of an examination image. As one example, the ultrasonography apparatus according to the present embodiment carries out a threshold process using the clarity detected (or calculated) from an examination image and a specified threshold and determines that the examination state is normal if the clarity exceeds the threshold (or if the clarity is equal to or greater than the threshold). The ultrasonography apparatus according to the present embodiment may also determine for example that the examination state is not normal if, as a result of the threshold process, the clarity is equal to or below the threshold (or the clarity is simply below the threshold).

Here, a detection level of outlines detected from the examination image can be given as one example of the clarity of the examination image according to the present embodiment. As one example, the ultrasonography apparatus according to the present embodiment detects outlines from an examination image and classifies the detected outlines into a plurality of detection levels according to a threshold process or the like. The ultrasonography apparatus according to the present embodiment then sets the detection level of the outlines detected from the examination image as the clarity of the examination image. Note that the clarity of the examination image according to the present embodiment is not limited to this example. As another example, the ultrasonography apparatus according to the present embodiment is also capable of using the Nitka method, the Rudinger & Spiegler method, or the like to calculate an evaluation value relating to the sharpness of the examination image and setting the calculated evaluation value as the clarity of the examination image.

Also, the ultrasonography apparatus according to the present embodiment may carry out image processing on an examination image as preprocessing that detects (or calculates) the clarity from the detection image. Here, the ultrasonography apparatus according to the present embodiment may change the content of the image processing on the examination image according to the subject and/or the examined part of the subject, for example.

As specific examples, when processing an examination image that shows a fetus (one example of a subject) or when processing an examination image showing the heart and blood vessels (one example of an examined part of a subject), the ultrasonography apparatus according to the present embodiment may carry out video processing such as motion compensation to cope with the movement of the fetus and pulsing of the heart. Also, when processing an examination image showing the liver, gallbladder, pancreas, spleen, uterus, thyroid, or the like (examples of examined parts of a subject), since the examined parts are substantially stationary, the ultrasonography apparatus according to the present embodiment may for example carry out a contrast enhancement process and still image processing such as outline extraction process and edge processing. Also, the ultrasonography apparatus according to the present embodiment may change the content of noise processing when carrying out the video processing described above and when carrying out the still image processing described above. When carrying out the video processing described above, as one example the ultrasonography apparatus according to the present embodiment reduces noise by averaging corresponding pixel values in a plurality of still images (frame images) that compose the video and are consecutive in time. When carrying out the still image processing described above, as one example the ultrasonography apparatus according to the present embodiment may reduce noise by carrying out an interpolation process.

As one example, by carrying out image processing on an examination image as preprocessing that detects (or calculates) the clarity from the examination image, the ultrasonography apparatus according to the present embodiment is capable of further improving the determination precision of the examination state determination process.

Note that the examination state determination process carried out by the ultrasonography apparatus according to the present embodiment is not limited to the example described above. For example, the ultrasonography apparatus according to the present embodiment may also determine the applied state of a gel (or jelly) applied to the subject during an ultrasonographic examination based on an examination image.

FIGS. 2A to 2D and FIGS. 3A to 3C are diagrams useful in explaining one example of an examination image processed by the ultrasonography apparatus according to the present embodiment. FIGS. 2A to 2D show examples of examination images that change according to the applied state of gel applied to the subject and show examples of examination images for a case where the amount of gel applied to the subject is in a relationship "FIG. 2A>FIG. 2B>FIG. 2C>FIG. 2D". FIGS. 3A to 3C show other examples of examination images that change according to the applied state of gel applied to the subject and show examples of examination images for a case where the gel has been unevenly applied. Here, FIG. 3A shows an example of an examination image for a state where there has been contact at both ends (i.e., the middle is missing). FIG. 3B shows an example of an examination image for a state where the left end is slightly prominent and FIG. 3C shows an example of an examination image for a state where the left end is prominent.

As shown in FIGS. 2A to 2D and FIGS. 3A to 3C, the examination images change according to the applied state of the gel applied to the subject. The ultrasonography apparatus according to the present embodiment may determine the applied state of the gel based on reference images showing various applied states of gel and an examination image.

For example, by further carrying out an examination state determination process such as that described above, the ultrasonography apparatus according to the present embodiment is capable, in the processing (frequency setting process) in (1) described above, of achieving the calibration of frequency mentioned earlier. Also, by carrying out the examination state determination process, the ultrasonography apparatus according to the present embodiment is capable of also realizing the processing shown in the first to fifth examples given below.

1. Processing Relating to a First Example: Frequency Adjusting Process

The ultrasonography apparatus according to the present embodiment adjusts the set frequency based on the determination result of the examination state in the examination state determination process described above (frequency adjusting process).

FIG. 4 is a flowchart showing one example of processing relating to the ultrasonography method according to the present embodiment. FIG. 4 shows one example of the processing of the ultrasonography method according to the present embodiment for a case where the ultrasonography apparatus according to the present embodiment carries out an adjusting process for the frequency. Here, the processing in step S100 shown in FIG. 4 corresponds to the processing (frequency setting process) in (1) described above and the processing in step S102 shown in FIG. 4 corresponds to the processing (sound wave generation control process) in (2) described above.

The ultrasonography apparatus according to the present embodiment sets a suitable frequency for the subject based on the subject information (S100).

When the frequency has been set in step S100, the ultrasonography apparatus according to the present embodiment causes the probe to generate sound waves of the set frequency (S102).

The ultrasonography apparatus according to the present embodiment adjusts the frequency based on an examination image that is an image showing echoes produced from the subject as the result of the sound waves generated in step S102 striking the subject (S104: frequency adjusting process).

FIG. 5 is a flowchart showing one example of the frequency adjusting process according to the present embodiment.

The ultrasonography apparatus according to the present embodiment determines whether to adjust the frequency based on an examination image (S200). More specifically, the ultrasonography apparatus according to the present embodiment carries out the examination state determination process described above based on the examination image.

As one example, the ultrasonography apparatus according to the present embodiment determines that the frequency is to be adjusted if the result of the examination state determination process based on the examination image does not indicate that "the examination state is normal" and determines that the frequency is not to be adjusted if the result of the examination state determination process described above indicates that "the examination state is normal".

On determining that the frequency is not to be adjusted in step S200, the ultrasonography apparatus according to the present embodiment ends the frequency adjusting process according to the present embodiment.

Meanwhile, on determining that the frequency is to be adjusted in step S200, the ultrasonography apparatus according to the present embodiment lowers the set frequency by a specified amount (S202). Here, the specified amount by which the ultrasonography apparatus according to the present embodiment adjusts the frequency may be a fixed value set in advance or may be a variable value that can be changed by the user (for example, the examiner) or the like of the ultrasonography apparatus according to the present embodiment.

After the processing in step S202, the ultrasonography apparatus according to the present embodiment determines whether to end the frequency adjusting process according to the present embodiment (S204). The ultrasonography apparatus according to the present embodiment carries out the examination state determination process described above based on an examination image obtained by sound waves of the changed frequency. As one example, the ultrasonography apparatus according to the present embodiment may then determine to continue the adjusting of frequency if the result of the examination state determination process based on the examination image does not indicate that "the examination state is normal" and to end the adjusting of frequency if the result of the examination state determination process described above indicates that "the examination state is normal".

On determining in step S204 to end the adjusting of frequency, the ultrasonography apparatus according to the present embodiment ends the frequency adjusting process according to the present embodiment.

Conversely, on determining in step S204 to continue the adjusting of frequency, the ultrasonography apparatus according to the present embodiment determines whether the contrast of the examination image is higher than the contrast of the examination image before the frequency was changed in step S202 (S206). Note that although an example where the ultrasonography apparatus according to the present embodiment makes the determination in step S206 in FIG. 5 based on the contrast of examination images is given here, the processing of the ultrasonography apparatus according to the present embodiment is not limited to this example. As another example, in step S206 the ultrasonography apparatus according to the present embodiment may carry out the determination based on another criterion obtained from an examination image, such as the clarity of the examination image. An example where the ultrasonography apparatus according to the present embodiment makes the determination based on the contrast of examination images as shown in FIG. 5 is given in the following description.

On determining in step S206 that the contrast of the examination image has increased, the ultrasonography apparatus according to the present embodiment repeats the processing from step S202.

Meanwhile, on determining in step S206 that the contrast of the examination image has not increased, the ultrasonography apparatus according to the present embodiment raises the set frequency by a specified amount (S208).

After carrying out the processing in step S208, the ultrasonography apparatus according to the present embodiment determines, in the same way as in step S204, whether to end the frequency adjusting process according to the present embodiment (S210).

On determining in step S210 to end the adjusting of frequency, the ultrasonography apparatus according to the present embodiment ends the frequency adjusting process according to the present embodiment.

Conversely, on determining in step S210 to continue the adjusting of frequency, the ultrasonography apparatus according to the present embodiment determines, in the same way as in step S206, whether the contrast of the examination image is higher than the contrast of the examination image before the frequency was changed in step S208 (S212).

On determining in step S212 that the contrast of the examination image has increased, the ultrasonography apparatus according to the present embodiment repeats the processing from step S208.

Meanwhile, on determining in step S212 that the contrast of the examination image has not increased, the ultrasonography apparatus according to the present embodiment ends the frequency adjusting process according to the present embodiment.

The ultrasonography apparatus according to the present embodiment carries out the processing shown in FIG. 5, for example, as the frequency adjusting process according to the present embodiment. By carrying out the processing shown in FIG. 5 for example, the ultrasonography apparatus according to the present embodiment is capable of raising the probability of obtaining an examination image for which the result of the examination state determination process described above is "the examination state is normal".

Note that the frequency adjusting process according to the present embodiment is not limited to the processing shown in FIG. 5. For example, the ultrasonography apparatus according to the present embodiment may adjust the frequency in the downward direction after first adjusting the frequency in the upward direction.

The description now returns to the example of processing relating to the ultrasonography method according to the present embodiment shown in FIG. 4. Once the frequency adjusting process in step S104 has ended, the ultrasonography apparatus according to the present embodiment determines whether to end the examination (S106). As one example, the ultrasonography apparatus according to the present embodiment determines whether to end the examination based on a user operation by a user or the like of the ultrasonography apparatus according to the present embodiment.

On determining in step S106 to continue the examination, the ultrasonography apparatus according to the present embodiment repeats the processing from step S102. Conversely, on determining in step S106 to end the examination, the ultrasonography apparatus according to the present embodiment ends the processing relating to the ultrasonography method according to the present embodiment.

The ultrasonography apparatus according to the present embodiment carries out the processing shown in FIG. 4, for example, as the processing relating to the ultrasonography method according to the present embodiment. By carrying out the processing shown in FIG. 4 for example, the ultrasonography apparatus according to the present embodiment is capable, via the frequency adjusting process according to the present embodiment, of raising the probability of obtaining an examination image for which the result of the examination state determination process described above is "the examination state is normal". Accordingly, by carrying out the processing shown in FIG. 4 for example, the ultrasonography apparatus according to the present embodiment is capable of raising the probability that an examiner will be able to carry out an ultrasonographic examination using sound waves of a suitable frequency for the subject.

2. Processing Relating to Second Example: Notification Control Process

The ultrasonography apparatus according to the present embodiment causes a notification unit (described later) provided in the ultrasonography apparatus and/or an external apparatus, for example, to give notification based on a determination result for the examination state produced in the examination state determination process described above (notification control process).

As examples of the notification method according to the present embodiment, it is possible to use a method that appeals to the user's senses, such as a visual notification method that uses characters, images, the illumination of lamps or the like or an audible method that uses audio (which hereinafter includes, music and sounds such as beeps). As specific examples of the notification method according to the present embodiment, it is possible to illuminate lamps corresponding to a notification content out of lamps of a plurality of colors corresponding to different notification contents or to change how lamp flash in accordance with the notification content (examples of visual notification methods). As another specific example of the notification method according to the present embodiment, it is possible to reproduce audio corresponding to the notification content out of audio corresponding to different notification contents (one example of an audible notification method).

A determination result for the examination state in the examination state determination process described above, such as "the examination state is normal" or "the examination state is not normal", can be given as an example of the notification content according to the present embodiment. Note that the notification content according to the present embodiment is not limited to the determination result for the examination state produced in the examination state determination process described above. As one example, if the ultrasonography apparatus according to the present embodiment determines the applied state of gel based on an examination image in the examination state determination process described above, it is possible to give notification of the applied state of gel applied to the subject in an ultrasonographic examination.

When causing a notification unit (described later) to give notification, as one example the ultrasonography apparatus according to the present embodiment causes the notification unit to give notification based on the determination result for the examination state in the examination state determination process described above by transmitting a control signal (or control data) controlling notification to the notification unit. Here, as one example, the control signal or control data controlling notification according to the present embodiment includes a notification instruction for having notification carried out. The control signal or control data controlling notification according to the present embodiment may also include data (such as image data or audio data) showing the notification content, for example.

When causing an external apparatus to give notification, as one example the ultrasonography apparatus according to the present embodiment causes the external apparatus to give notification based on the determination result for the examination state in the examination state determination process by transmitting control data for controlling notification to the external apparatus which is connected via a network (or directly) using a wired or wireless connection. Here, a wired network such as a LAN (Local Area Network) or a WAN (Wide Area Network, a wireless network such as a WLAN (Wireless Local Area Network), or the Internet which uses a communication protocol such as TCP/IP (Transmission Control Protocol/Internet Protocol) can be given as examples of a "network" for the present embodiment.

By carrying out a notification control process such as that described above, the ultrasonography apparatus according to the present embodiment enables the examiner, for example, to grasp the present state of an ultrasonographic examination and thereby enables the examiner to improve the examination state. That is, the notification realized by the notification control process according to the present embodiment corresponds to feeding back the present state of an ultrasonographic examination to an examiner or the like. Accordingly, by carrying out the notification control process described above (which corresponds to a feedback process), the ultrasonography apparatus according to the present embodiment is capable of increasing the precision of an ultrasonographic examination carried out by an examiner using sound waves of a suitable frequency for the subject.

Note that the notification control process carried out by the ultrasonography apparatus according to the present embodiment is not limited to the processing described above. Another example of the notification control process carried out by the ultrasonography apparatus according to the present embodiment will be described later as "Processing Relating to a Fourth Example".

FIG. 6 is a flowchart showing another example of processing relating to the ultrasonography method according to the present embodiment. FIG. 6 shows one example of processing relating to the ultrasonography method according to the present embodiment for a case where the ultrasonography apparatus according to the present embodiment carries out a notification control process. Here, the processing in step S300 shown in FIG. 6 corresponds to the processing (frequency setting process) in (1) described above and the processing in step S302 shown in FIG. 6 corresponds to the processing (sound wave generation control process) in (2) described above. The processing in step S306 shown in FIG. 6 corresponds to the notification control process described above.

The ultrasonography apparatus according to the present embodiment sets a suitable frequency for the subject based on the subject information (S300).

When the frequency has been set in step S300, the ultrasonography apparatus according to the present embodiment causes the probe to generate sound waves of the set frequency (S302).

After carrying out the processing in step S302, the ultrasonography apparatus according to the present embodiment determines whether to give feedback to the examiner or the like (S304). As one example, if the ultrasonography apparatus according to the present embodiment has been set so as to carry out the notification control process according to the present embodiment, the ultrasonography apparatus determines to give feedback.

On determining to not give feedback to the examiner or the like in step S304, the ultrasonography apparatus according to the present embodiment carries out the processing in step S308, described later.

Conversely, on determining to give feedback to the examiner or the like in step S304, the ultrasonography apparatus according to the present embodiment causes a notification unit (described later) and/or an external apparatus to give notification (S306). As a specific example, the ultrasonography apparatus according to the present embodiment carries out the examination state determination process described above based on an examination image obtained by sound waves generated in step S302. The ultrasonography apparatus according to the present embodiment then carries out the processing in step S306 by transmitting control data, which controls notification corresponding to the result of the examination state determination process described above based on an examination image, to the notification unit and/or to the external apparatus.

After deciding in step S304 to not give feedback to the examiner or the like or after carrying out the processing in step S306, in the same way as in step S106 in FIG. 2, the ultrasonography apparatus according to the present embodiment determines whether to end the examination (S308).

On determining in step S308 to continue the examination, the ultrasonography apparatus according to the present embodiment repeats the processing from step S302. On determining to end the examination in step S308, the ultrasonography apparatus according to the present embodiment ends the processing relating to the ultrasonography method according to the present embodiment.

The ultrasonography apparatus according to the present embodiment carries out the processing shown in FIG. 6, for example, as the processing relating to the ultrasonography method according to the present embodiment. If the processing shown in FIG. 6 is carried out, through the notification control process according to the present embodiment, the ultrasonography apparatus according to the present embodiment has notification given relating to the present state of an ultrasonographic examination (a notification based on the determination result for the examination state in the examination state determination process described above, one example of feedback). Accordingly, as one example, an examiner who has received the notification caused by the ultrasonography apparatus according to the present embodiment will be capable of grasping the present state of an ultrasonographic examination and thereby able to improve the examination state. Accordingly, by carrying out the processing shown in FIG. 6 for example, the ultrasonography apparatus according to the present embodiment is capable of improving the precision of an ultrasonographic examination carried out by an examiner using sound waves of a suitable frequency for the subject.

3. Processing Relating to a Third Example: Recording Control Process

The ultrasonography apparatus according to the present embodiment selectively records reference determination state information showing a state where an examination is being carried out normally based for example on the determination result for an examination state in the examination state determination process described above (recording control process). As a specific example, the ultrasonography apparatus according to the present embodiment records reference examination state information on a recording medium when the result of the examination state determination process based on an examination image indicates that "the examination state is normal". The ultrasonography apparatus according to the present embodiment does not record reference examination state information on the recording medium for example when the result of the examination state determination process based on an examination image does not indicate that "the examination state is normal".

Here, data showing the position (examination position) of the probe and/or the inclination of the probe when the result of the examination state determination process described above indicates that "the examination state is normal" can be given as one example of reference examination state information for the present embodiment. A method of specifying the position (examination position) of the probe and the inclination of the probe carried out by the ultrasonography apparatus according to the present embodiment will be described later.

Note that the reference examination state information according to the present embodiment is not limited to the example described above. As one example, if the probe according to the present embodiment is equipped with a pressure sensor, data showing the pressure value of the probe that is acquired from the probe at a time when the result of the examination state determination process described above indicates that "the examination state is normal" may be included in the reference examination state information according to the present embodiment.

Here, a storage unit (described later) provided in the ultrasonography apparatus according to the present embodiment, a removable external recording medium that is connected to the ultrasonography apparatus according to the present embodiment, and a recording medium provided in an external apparatus which is connected via a network (or directly) to the ultrasonography apparatus according to the present embodiment using a wired or wireless connection can be given as specific examples of a recording medium on which the ultrasonography apparatus according to the present embodiment records the reference examination state information. If the reference examination state information is stored on a recording medium provided in an external apparatus, as one example the ultrasonography apparatus according to the present embodiment stores the reference examination state information on the recording medium provided in the external apparatus by transmitting the reference examination state information and a recording instruction for having the reference examination state information recorded to the external apparatus.

As described above, the reference examination state information for the present embodiment shows the examination position (probe position), and/or the inclination of the probe and the like in a state where a normal examination is being carried out. Accordingly, by recording the reference examination state information on a recording medium, the ultrasonography apparatus according to the present embodiment becomes capable of further realizing processing (for example, the processing relating to the fourth example described later (notification control process)) that uses the reference examination state information and has a state where a normal examination is being carried out as a reference. Also by recording the reference examination state information on a recording medium, the ultrasonography apparatus according to the present embodiment is capable for example of causing an external apparatus to carry out processing (for example, processing that is the same as the processing relating to the fourth example described later) that uses the reference examination state information and has a state where a normal examination is being carried out as a reference.

Note that although the reference examination state information according to the present embodiment is recorded by the ultrasonography apparatus according to the present embodiment carrying out a recording control process when an actual ultrasonographic examination is carried out on a patient or the like receiving an ultrasonographic examination, the reference examination state information according to the present embodiment is not limited to this example. For example, the reference examination state information according to the present embodiment may be recorded by the ultrasonography apparatus according to the present embodiment carrying out the recording control process when a provisional ultrasonographic examination for recording the reference examination state information is carried out by a highly proficient examiner or the like.

Here, an example of a method of specifying the position of the probe (examination position) and the inclination of the probe carried out by the ultrasonography apparatus according to the present embodiment will be described.

3-1. Processing Relating to a First Specifying Method

As one example, the ultrasonography apparatus according to the present embodiment specifies the position of the probe (examination position) and the inclination of the probe based on a picked-up image produced by photographing the subject and a probe provided with a marker.

FIG. 7 is a flowchart showing a first example of processing relating to a method of specifying the position of the probe (examination position) and the inclination of the probe according to the present embodiment. Here, FIG. 7 shows one example of processing by which the ultrasonography apparatus according to the present embodiment specifies the position of the probe (examination position) and the inclination of the probe based on an image signal (image data) that shows the picked-up image and was transmitted from an image pickup apparatus that photographs the subject and the probe that is provided with a marker.

The ultrasonography apparatus according to the present embodiment detects outlines of the subject based on a template image corresponding to the subject (for example, a human form template image) and the picked-up image (S400). Here, as one example, the ultrasonography apparatus according to the present embodiment reads a template image corresponding to the subject from the storage unit (described later) based on the subject information specified in the processing (frequency setting process) in (1) described above. As another example, the ultrasonography apparatus according to the present embodiment may acquire a template image corresponding to the subject from an external apparatus based on the subject information described above.

The ultrasonography apparatus according to the present embodiment specifies the position of the subject based on the detection result in step S400 (S402). Here, the processing of step S402 corresponds for example to processing that sets reference coordinate axes for specifying the position (examination position) of the probe.

The ultrasonography apparatus according to the present embodiment detects the marker provided on the probe based on the picked-up image (S404).

The ultrasonography apparatus according to the present embodiment specifies the position of the probe based on the position of the subject specified in step S402 and the marker detected in step S404 (S406). The ultrasonography apparatus according to the present embodiment carries out the processing in step S406 by deciding the coordinates of the detected marker on the reference coordinate axes set in step S404, for example.

Also, the ultrasonography apparatus according to the present embodiment specifies the inclination of the x, y, and z axis directions of the probe on the reference coordinate axes set in step S404 based on the form of the marker detected in step S404. As one example, the ultrasonography apparatus according to the present embodiment carries out the processing in step S408 by estimating the inclination of the x, y, and z axes of the probe based on the data showing a standard form of the marker and the form of the marker detected based in a picked-up image.

Note that although an example where the processing in step S408 is carried out after the processing in step S406 has been carried out is shown in FIG. 7, the ultrasonography apparatus according to the present embodiment is also capable of executing the processing in step S406 and the processing in step S408 independently. Accordingly, as examples, the ultrasonography apparatus according to the present embodiment may carry out the processing in step S406 after the processing in step S408 or may carry out the processing in step S406 and the processing in step S408 in synchronization.

As a result of the processing in steps S406 and S408, the position and inclination of the probe at a given time are specified.

When the processing in steps S406 and S408 has been completed, the ultrasonography apparatus according to the present embodiment determines whether to end the detection of the position and inclination of the probe (S410). As one example, the ultrasonography apparatus according to the present embodiment determines whether to end the detection of the position and inclination of the probe based on a user operation by the user or the like of the ultrasonography apparatus according to the present embodiment.

On determining in step S410 to continue the detection of the position and inclination of the probe, the ultrasonography apparatus according to the present embodiment repeats the processing from step S404. Conversely, on determining in step S410 to end the detection of the position and inclination of the probe, the ultrasonography apparatus according to the present embodiment ends the processing relating to the method of specifying the position of the probe (examination position) and the inclination of the probe.

By carrying out the processing shown in FIG. 7 for example, the ultrasonography apparatus according to the present embodiment is capable of specifying the position of the probe (examination position) and the inclination of the probe at each given time.

3-2. Processing Relating to a Second Specifying Method

Note that the processing relating to the method of specifying the position of the probe (examination position) and the inclination of the probe carried out by the ultrasonography apparatus according to the present embodiment is not limited to the processing relating to the first example shown in FIG. 7. For example, if the probe is equipped with an angular velocity sensor and a triaxial acceleration sensor, the ultrasonography apparatus according to the present embodiment is also capable of specifying the position of the probe (examination position) and the inclination of the probe based on an examination image and the detected values of such sensors obtained from the probe.

FIG. 8 is a flowchart showing a second example of processing relating to a method of specifying the position of the probe (examination position) and the inclination of the probe according to the present embodiment. Here, FIG. 8 shows one example of processing by which the ultrasonography apparatus according to the present embodiment specifies the position of the probe (examination position) and the inclination of the probe based on an examination image and on a detected value of an angular velocity sensor and a detected value of an acceleration sensor obtained from the probe.

The ultrasonography apparatus according to the present embodiment detects the inclination of the probe relative to a surface of the subject (for example, the body surface) based on an examination image (S500). As one example, the ultrasonography apparatus according to the present embodiment carries out the processing in step S500 by detecting a line of the surface of the subject (for example, the body surface) based on the examination image.

The ultrasonography apparatus according to the present embodiment specifies the examination position of the subject based on the form of the surface of the subject detected in step S500 and a template image corresponding to the subject (for example, a human form template image) (S502). Here, as one example, the ultrasonography apparatus according to the present embodiment acquires the template image corresponding to the subject in the same way as in step S400 shown in FIG. 7. The processing in step S502 corresponds to processing that sets reference coordinate axes for specifying the position of the probe (examination position), for example.

The ultrasonography apparatus according to the present embodiment detects inclination of the probe relative to the horizontal plane based on a detected value of the angular velocity sensor provided in the probe and carries out angular correction (S504). The ultrasonography apparatus according to the present embodiment also calculates the moved distance of the probe based on the detected value of the acceleration sensor provided in the probe (S506). As one example, the ultrasonography apparatus according to the present embodiment carries out the processing in step S506 by integrating detected values of the acceleration sensor to calculate speed and then further integrating the calculated speed.

Note that although FIG. 8 shows an example where the processing in step S506 is carried out after the processing in step S504 has been carried out, the ultrasonography apparatus according to the present embodiment is also capable of executing the processing in step S504 and the processing in step S506 independently. Accordingly, as examples, the ultrasonography apparatus according to the present embodiment may carry out the processing in step S504 after the processing in step S506 or may carry out the processing in step S504 and the processing in step S506 in synchronization.

Once the processing in steps S504 and S506 has been completed, the ultrasonography apparatus according to the present embodiment specifies the position of the probe relative to the subject and the inclination of the probe relative to the subject based on the result of the processing in step S504 and the result of the processing in step S506 (S508). According to the processing in step S508, the position of the probe relative to the subject and the inclination of the probe relative to the subject at a given time are specified.

When the processing in step S508 has been completed, the ultrasonography apparatus according to the present embodiment determines whether to end the detection of the position and inclination of the probe in the same way as in step S410 in FIG. 7 (S510).

On determining in step S510 to continue the detection of the position and inclination of the probe, the ultrasonography apparatus according to the present embodiment repeats the processing from step S504. Conversely, on determining in step S510 to end the detection of the position and inclination of the probe, the ultrasonography apparatus according to the present embodiment ends the processing relating to the method of specifying the position of the probe (examination position) and the inclination of the probe.

By carrying out the processing shown in FIG. 8 for example, the ultrasonography apparatus according to the present embodiment is capable of specifying the position of the probe (examination position) and the inclination of the probe at each given time.

3-3. Processing Relating to a Third Specifying Method

Note that the processing relating to the method of specifying the position of the probe (examination position) and the inclination of the probe carried out by the ultrasonography apparatus according to the present embodiment is not limited to the processing relating to the first example shown in FIG. 7 or the processing relating to the second example shown in FIG. 8. For example, if the probe is equipped with an angular velocity sensor and a triaxial acceleration sensor, the ultrasonography apparatus according to the present embodiment is also capable of specifying the position of the probe (examination position) and the inclination of the probe based on the detected values of such sensors obtained from the probe.

FIG. 9 is a flowchart showing a third example of processing relating to a method of specifying the position of the probe (examination position) and the inclination of the probe according to the present embodiment. Here, FIG. 9 shows one example of processing by which the ultrasonography apparatus according to the present embodiment specifies the position of the probe (examination position) and the inclination of the probe based on detected values of the angular velocity sensor and detected values of the acceleration sensor obtained from the probe.

The ultrasonography apparatus according to the present embodiment instructs the examiner to press the probe at a specified angle at a specified examination position on the subject for a set time (S600). The ultrasonography apparatus also sets initial values of the position of the probe and the inclination of the probe based on detected values of the angular velocity sensor provided in the probe and detected values of the acceleration sensor provided in the probe (S602). On determining, based on the detected values of the sensors described above, that the probe has not moved for the set time relating to the instruction given in step S600, the ultrasonography apparatus according to the present embodiment sets the specified examination position and the specified angle relating to the instruction given in step S600 as initial values. Here, the processing in steps S600 and S602 corresponds for example to processing that sets reference coordinate axes for specifying the position of the probe (examination position).

Once the initial values of the position of the probe and the inclination of the probe have been set in step S602, the ultrasonography apparatus according to the present embodiment detects the inclination of the probe relative to a horizontal plane based on a detected value of the angular velocity sensor provided in the probe and carries out angular correction (S604). The ultrasonography apparatus according to the present embodiment also calculates the moved distance of the probe based on the detected value of the acceleration sensor provided in the probe in the same way as in step S506 in FIG. 8, for example (S606).

Note that although FIG. 9 shows an example where the processing in step S606 is carried out after the processing in step S604 has been carried out, the ultrasonography apparatus according to the present embodiment is also capable of executing the processing in step S604 and the processing in step S606 independently. Accordingly, as examples, the ultrasonography apparatus according to the present embodiment may carry out the processing in step S604 after the processing in step S606 or may carry out the processing in step S604 and the processing in step S606 in synchronization.

Once the processing in steps S604 and S606 has been completed, the ultrasonography apparatus according to the present embodiment specifies the position of the probe relative to the subject and the inclination of the probe relative to the subject based on the result of the processing in step S604 and the result of the processing in step S606 (S608). According to the processing in step S608, the position of the probe relative to the subject and the inclination of the probe relative to the subject at a given time are specified.

When the processing in step S608 has been completed, the ultrasonography apparatus according to the present embodiment determines whether to end the detection of the position and inclination of the probe in the same way as in step S410 in FIG. 7 (S610).

On determining in step S610 to continue the detection of the position and inclination of the probe, the ultrasonography apparatus according to the present embodiment repeats the processing from step S604. Conversely, on determining in step S610 to end the detection of the position and inclination of the probe, the ultrasonography apparatus according to the present embodiment ends the processing relating to the method of specifying the position of the probe (examination position) and the inclination of the probe.

By carrying out the processing shown in FIG. 9 for example, the ultrasonography apparatus according to the present embodiment is capable of specifying the position of the probe (examination position) and the inclination of the probe at each given time.

As examples, by carrying out the processing relating to the first example described above, the processing relating to the second example described above, or the processing relating to the third example described above, the ultrasonography apparatus according to the present embodiment specifies the position of the probe (examination position) and the inclination of the probe. Note that it should be obvious that the processing relating to the method of specifying the position of the probe (examination position) and the inclination of the probe carried out by the ultrasonography apparatus according to the present embodiment is not limited to the processing relating to the first to third examples described above.

4. Processing Relating to a Fourth Example: Notification Control Process

If, for example, the determination result for the examination state in the examination state determination process described above does not indicate that a normal examination is being carried out, the ultrasonography apparatus according to the present embodiment causes a notification unit (described later) and/or an external apparatus to give notification based on reference examination state information stored on a recording medium by the recording control process described above and on examination state information showing the examination state (notification control process).

Here, data showing the position of the probe (examination position) and/or the inclination of the probe at a given time during an ultrasonographic examination can be given as an example of the examination state information for the present embodiment. Note that the examination state information for the present embodiment is not limited to this example. As another example, if the probe according to the present embodiment is equipped with a pressure sensor, the examination state information according to the present embodiment may include data showing a pressure value of the probe acquired from the probe at a given time during the ultrasonographic examination. That is, the examination state information according to the present embodiment includes data corresponding to reference examination state information for the present embodiment at a given time during an ultrasonographic examination.

Here, content (orientation content) that gives guidance about the position and/or inclination of the probe to produce a normal examination state can be given as one example of notification content based on the reference examination state information and examination state information for the present embodiment. As one example, the ultrasonography apparatus according to the present embodiment guides the position and/or orientation of the probe so that the position and/or orientation of the probe, the pressure value, and the like shown by the examination state information match the position and/or orientation, the pressure value, and the like shown by the reference examination state information.

When causing a notification unit to give notification, as one example the ultrasonography apparatus according to the present embodiment causes the notification unit to give notification based on reference examination state information and examination state information by transmitting a control signal (or control data) for controlling notification to the notification unit. When causing an external apparatus to give notification, as one example the ultrasonography apparatus according to the present embodiment causes the external apparatus to give notification based on reference examination state information and examination state information by transmitting control data for controlling notification to the external apparatus which is connected via a network (or directly) using a wired or wireless connection.

By having notification given based on the reference examination state information and the examination state information, the ultrasonography apparatus according to the present embodiment enables the examiner for example to improve the examination state.

By having notification given based on the reference examination state information and the examination state information, the ultrasonography apparatus according to the present embodiment is capable of giving guidance about the position and/or inclination of the probe. Accordingly, even in an imaginary case where the examiner has limited examination skills, the ultrasonography apparatus according to the present embodiment is capable of enabling the examiner to carry out a normal ultrasonographic examination (an ultrasonographic examination where the result of the examination state determination process described above is "the examination state is normal").

Accordingly, by carrying out the notification control process (which also corresponds to a feedback process) as described above, the ultrasonography apparatus according to the present embodiment is capable of improving the precision of an ultrasonographic examination carried out by the examiner using sound waves of a suitable frequency for the subject.

5. Processing Relating to a Fifth Example

Processing that can be realized by the ultrasonography apparatus according to the present embodiment carrying out the examination state determination process in addition to the processing (frequency setting process) in (1) described above and the processing (sound wave generation control process) in (2) described above is not limited to the processing relating to the first to fourth examples described above. For example, the ultrasonography apparatus according to the present embodiment is also capable of carrying out processing that is a combination of a plurality of processing out of processing relating to the first to fourth examples described above.

Ultrasonography Apparatus According to the Present Embodiment

Next, one example configuration of an ultrasonography apparatus according to the present embodiment that is capable of carrying out processing relating to the ultrasonography method according to the present embodiment described above will be described.

FIG. 10 is a block diagram showing one example of the configuration of an ultrasonography apparatus 100 according to the present embodiment. Here, FIG. 10 also shows a probe 200 according to the present embodiment as an external apparatus for the ultrasonography apparatus 100.

As one example, the ultrasonography apparatus 100 includes a control unit 102 and a notification unit 104.

Also, the ultrasonography apparatus 100 may also include a ROM (Read Only Memory, not shown), a RAM (Random Access Memory, not shown), a storage unit (not shown), an operation unit capable of being operated by a user (not shown), a display unit displaying a variety of screens on a display screen (not shown), a communication unit (not shown), and the like. In the ultrasonography apparatus 100, as one example the respective component elements are connected by a bus as a data transfer path.

Here, the ROM (not shown) stores a program used by the control unit 102 and control data such as calculation parameters. The RAM (not shown) temporarily stores a program or the like executed by the control unit 102.

The storage unit (not shown) is a storage device provided in the ultrasonography apparatus 100 and as examples stores the reference examination state information and various data such as applications. Here, a magnetic recording medium such as a hard disk, an EEPROM (Electrically Erasable and Programmable Read Only Memory), and a nonvolatile memory such as a flash memory can be given as examples of the storage unit (not shown). The storage unit (not shown) may also be removable from the ultrasonography apparatus 100.

A button or buttons, arrow keys, a rotary selector such as a jog dial, or a combination of the same can be given as examples of the operation unit (not shown). Note that the ultrasonography apparatus 100 may also be connected to an external operation device such as an operation input device (such as a keyboard or a mouse) as an external apparatus for the ultrasonography apparatus 100.

The display unit (not shown) is a display device provided in the ultrasonography apparatus 100 and displays various information (such as images and/or characters) on a display screen. An operation screen and the like for having a desired operation carried out by the ultrasonography apparatus 100 can be given as an example of a screen displayed on the display screen of the display unit (not shown). The display unit may also serve as the notification unit 104.

Here, as the display unit, as examples it is possible to use a display device such as an LCD (Liquid Crystal Display), an organic EL (Electro-Luminescence) display, or an OLED (Organic Light Emitting Diode) display. It is also possible to construct the display unit of the ultrasonography apparatus 100 using a touch screen, for example. In such case, the display unit (not shown) functions as an operation display unit capable of both user operations and displaying.

The communication unit (not shown) is a communication device provided in the ultrasonography apparatus 100 and communicates via a network (or directly) with an external apparatus such as a server either wirelessly or using wires. Here, a communication antenna and an RF (Radio Frequency) circuit (wireless communication), an IEEE802.15.1 port and a transmission/reception circuit (wireless communication), an IEEE802.11b port and a transmission/reception circuit (wireless communication), or a LAN terminal and a transmission/reception circuit (wired communication) can be given as examples of the communication unit.

Example Hardware Configuration of Ultrasonography Apparatus 100

FIG. 11 is a diagram useful in explaining one example of the hardware configuration of the ultrasonography apparatus 100 according to the present embodiment. Here, FIG. 11 also shows the probe 200 as an external apparatus for the ultrasonography apparatus 100.

As one example, the ultrasonography apparatus 100 includes an MPU 150, a ROM 152, a RAM 154, a recording medium 156, an input/output interface 158, an operation input device 160, a display device 162, and a communication interface 164. In the ultrasonography apparatus 100, as one example the respective component elements are connected by a bus 166 as a data transfer path.

The MPU 150 is constructed of an MPU (Micro Processing Unit) or various processing circuits, for example, and functions as the control unit 102 that controls the entire ultrasonography apparatus 100. In the ultrasonography apparatus 100, as one example the MPU 150 serves as a frequency setting unit 110, a sound wave generation control unit 112, an examination state determining unit 114, a notification control unit 116, and a recording control unit 118, described later.

The ROM 152 stores a program and control data such as calculation parameters used by the MPU 150. The RAM 154 temporarily stores a program, which is executed by the MPU 150, and the like.

The recording medium 156 functions as the storage unit (not shown) and as examples stores the reference examination state information and a variety of data such as applications. Here, a magnetic storage medium such as a hard disk and a nonvolatile memory such as a flash memory can be given as examples of the recording medium 156. The recording medium 156 may be removable from the ultrasonography apparatus 100.

As examples, the input/output interface 158 is connected to the operation input device 160 and to the display device 162. The input/output interface 158 also serves so as to connect to an external apparatus such as the probe 200 or the like. The operation input device 160 functions as the operation unit (not shown) and the display device 162 functions as the display unit (not shown).

Here, a USB (Universal Serial Bus) terminal, a DVI (Digital Visual Interface) terminal, an HDMI (High-Definition Multimedia Interface) terminal, and various processing circuits can be given as examples of the input/output interface 158. As one example, the operation input device 160 is provided on the ultrasonography apparatus 100 and is connected to the input/output interface 158 inside the ultrasonography apparatus 100. A button or buttons, arrow keys, a rotary selector such as a jog dial, or a combination of the same can be given as examples of the operation input device 160. As one example, the display device 162 is also provided on the ultrasonography apparatus 100 and is connected to the input/output interface 158 inside the ultrasonography apparatus 100. A liquid crystal display and an organic EL display can be given as examples of the display device 162.

Note that it should be obvious that it is also possible for the input/output interface 158 to connect to external devices such as an operation input device (such as a keyboard or mouse) and/or a display device as external apparatuses for the ultrasonography apparatus 100. The display device 162 may be a device, such as a touch screen, capable of both user operations and displaying.

The communication interface 164 is a communication device provided in the ultrasonography apparatus 100 and functions as the communication unit (not shown) for communicating via a network (or directly) with an external apparatus such as a server either wirelessly or using wires. Here, a communication antenna and an RF (Radio Frequency) circuit (wireless communication), or a LAN terminal and a transmission/reception circuit (wired communication) can be given as examples of the communication interface 164.

By using the configuration shown in FIG. 11, for example, the ultrasonography apparatus 100 carries out processing relating to the ultrasonography method according to the present embodiment.

Note that the hardware configuration of the ultrasonography apparatus 100 according to the present embodiment is not limited to the configuration shown in FIG. 11. For example, the ultrasonography apparatus 100 may be provided with an image pickup device that serves as an image pickup unit (not shown) that picks up still images or video. If an image pickup device is provided, the ultrasonography apparatus 100 becomes capable of carrying out processing such as the processing relating to the first method of specifying described earlier based on a picked-up image generated by image pickup by the image pickup device, for example.

Here, a lens/image pickup element and signal processing circuit can be given as an example of the image pickup device according to the present embodiment. As one example, the lens/image pickup element is composed of lenses of an optical system and an image sensor using a plurality of image pickup elements such as CMOS (Complementary Metal Oxide Semiconductor). The signal processing circuit includes an AGC (Automatic Gain Control) circuit and an ADC (Analog to Digital Converter), converts an analog signal generated by the image pickup element to a digital signal (image data) and carries out various signal processing. A white balance correction process, a color correction process, a gamma correction process, a YCbCr conversion process, and an edge enhancing process can be given as examples of the signal processing carried out by the signal processing circuit.

The ultrasonography apparatus 100 may further include a DSP (Digital Signal Processor) and an audio output device. An amplifier and a speaker can be given as examples of an audio output device according to the present embodiment. Here if a DSP and an audio output device are provided, the DSP and the audio output device serve as the notification unit 104, for example.

If the ultrasonography apparatus 100 is configured so as to be capable of standalone processing, for example, the communication interface 164 does not need to be provided. It is also possible to configure the ultrasonography apparatus 100 so as to not include the operation input device 160 and/or the display device 162.

The description now returns to the example configuration of the ultrasonography apparatus 100 shown in FIG. 10. The control unit 102 is constructed of an MPU and/or various processing circuits for example and controls the entire ultrasonography apparatus 100. The control unit 102 includes the frequency setting unit 110, the sound wave generation control unit 112, the examination state determining unit 114, the notification control unit 116, and the recording control unit 118, for example, and takes the lead role in the processing relating to the ultrasonography method according to the present embodiment.

The frequency setting unit 110 takes the lead role in the processing (frequency setting process) in (1) described above and sets a suitable frequency for the subject based on the subject information. The frequency setting unit 110 may shift the set frequency in a range of frequencies specified based on the subject information and set a suitable frequency for the subject out of the shifted frequencies. As one example, the frequency setting unit 110 sets a suitable frequency for the subject out of the shifted frequencies based on a signal (or data) showing the determination result for the examination state transmitted from the examination state determining unit 114, described later.

Also, as one example, the frequency setting unit 110 may adjust the set frequency based on a signal (or data) showing the determination result for the examination state transmitted from the examination state determining unit 114, described later. That is, the frequency setting unit 110 may be able to take the lead role in the frequency adjusting process described above, for example.

The frequency setting unit 110 transmits a signal (or data) showing the set frequency (which for example may include a provisionally set frequency or a frequency being adjusted) to the sound wave generation control unit 112.

The sound wave generation control unit 112 takes the lead role in the processing (sound wave generation control process) in (2) described above and causes the probe 200 to generate sound waves of the frequency set by the frequency setting unit 110. More specifically, as one example, the sound wave generation control unit 112 applies a voltage corresponding to the signal showing the set frequency transmitted from the frequency setting unit 110 to the probe 200 to cause the probe 200 to generate sound waves of the set frequency.

The examination state determining unit 114 takes the lead role in the examination state determination process described above and determines the examination state based for example on the clarity of an examination image. Here, as one example, the examination state determining unit 114 may subject the examination image to image processing which is suitable for the subject or for the examined part of the subject based on a signal received from the probe 200 and determine the examination state based on the examination image after image processing.

Also, the examination state determining unit 114 transmits a signal (or data) showing the determination result for the examination state to the frequency setting unit 110, the notification control unit 116, and the recording control unit 118, for example. Note that the examination state determining unit 114 may selectively transmit a signal showing the determination result for the examination state to one or two or more component elements out of the frequency setting unit 110, the notification control unit 116, and the recording control unit 118 based on an operation signal based on a user operation transmitted from an operation unit (not shown), for example.

The notification control unit 116 takes the lead role in the notification control process described above and as one example causes the notification unit 104 and/or the external apparatus to give notification based on the determination result for the examination state produced by the examination state determining unit 114. Also, if the determination result for the examination state produced by the examination state determining unit 114 shows that a normal examination is not being carried out, for example, the notification control unit 116 may cause the notification unit 104 and/or the external apparatus to give notification based on reference examination state information and the examination state information.

The recording control unit 118 takes the lead role in the recording control process described above and selectively records reference examination state information based on the determination result for the examination state produced by the examination state determining unit 114, for example.

Here, a storage unit (not shown), a removable external recording medium that is connected to the ultrasonography apparatus 100, and a recording medium provided in an external apparatus connected via a network (or directly) to the ultrasonography apparatus 100 either wirelessly or using wires can be given as examples of the recording medium on which the recording control unit 118 records the reference examination state information. If the reference examination state information is recorded on a recording medium provided in an external apparatus, the recording control unit 118 has a communication unit (not shown) transmit the reference examination state information and a recording instruction for recording the reference examination state information to the external apparatus.

By including the frequency setting unit 110, the sound wave generation control unit 112, the examination state determining unit 114, the notification control unit 116, and the recording control unit 118, for example, the control unit 102 takes the lead role in the processing relating to the ultrasonography method according to the present embodiment.

Note that the configuration of the control unit according to the present embodiment is not limited to the above example. As another example, one or two or more of the examination state determining unit 114, the notification control unit 116, and the recording control unit 118 may be omitted from the control unit according to the present embodiment. Even when one or two or more of the examination state determining unit 114, the notification control unit 116, and the recording control unit 118 is/are omitted, the control unit according to the present embodiment is still capable of taking the lead role in the processing (frequency setting process) in (1) described above and the processing (sound wave generation control process) in (2) described above.

The notification unit 104 gives notification based on a control signal (or control data) for controlling notification transmitted from the notification control unit 116. That is, notification by the notification unit 104 is controlled by the notification control unit 116. Here, a display device that serves as a display unit (not shown), and a DSP and audio output device can be given as examples of the notification unit 104.

As one example, if a display device serves as the notification unit 104, the ultrasonography apparatus 100 is capable of notifying the examiner or the like using the visual notification methods described above. Also, if a DSP and audio output device serve as the notification unit 104, the ultrasonography apparatus 100 is capable of notifying the examiner or the like using the audible notification methods described above.

Note that the notification unit 104 according to the present embodiment is not limited to the display device described above and the DSP and audio output device described above.

As another example, the notification unit 104 may include an arbitrary device that realizes a method that appeals to the user's senses. As yet another example, the notification unit 104 may also be configured so as to be capable of realizing a plurality of notification methods, such as by including the display device described above and the DSP and audio output device described above.

By using the configuration shown in FIG. 10, for example, the ultrasonography apparatus 100 is capable of carrying out the processing (frequency setting process) in (1) described above and the processing (sound wave generation control process) in (2) described above relating to the ultrasonography method according to the present embodiment. Accordingly by using the configuration shown in FIG. 10, for example, the ultrasonography apparatus 100 is capable of enabling the examiner to carry out an ultrasonographic examination using sound waves of a suitable frequency for the subject.

By using the configuration shown in FIG. 10, for example, the ultrasonography apparatus 100 is also capable of carrying out the examination state determination process, the notification control process, and the recording control process described earlier. Accordingly, by using the configuration shown in FIG. 10, for example, the ultrasonography apparatus 100 is capable of carrying out the processing shown in the first to fifth examples described earlier, for example, and is capable of achieving the effects corresponding to the processing shown in the first to fifth examples described earlier.

Note that the configuration of the ultrasonography apparatus according to the present embodiment is not limited to the configuration shown in FIG. 10. As one example, the ultrasonography apparatus according to the present embodiment may be equipped with the probe according to the present embodiment. When equipped with the probe according to the present embodiment, the ultrasonography apparatus according to the present embodiment is capable of causing sound waves with a frequency controlled by the processing relating to the ultrasonography method according to the present embodiment to be generated from the included probe. Accordingly even with a configuration equipped with the probe according to the present embodiment, the ultrasonography apparatus according to the present embodiment is capable of achieving the same effects as the ultrasonography apparatus 100 shown in FIG. 10.

As another example, the ultrasonography apparatus according to the present embodiment may be configured so as to omit the notification unit 104. Even with a configuration that omits the notification unit 104, the ultrasonography apparatus according to the present embodiment is capable of carrying out the processing (frequency setting process) in (1) described above and the processing (sound wave generation control process) in (2) described above. Also, even with a configuration that does not include the notification unit 104, the ultrasonography apparatus according to the present embodiment is capable of notifying the examiner or the like by having an external apparatus, for example, carry out notification in the notification control process.

The ultrasonography apparatus according to the present embodiment can also be separately provided with one or two or more component elements out of the frequency setting unit 110, the sound wave generation control unit 112, the examination state determining unit 114, the notification control unit 116, and the recording control unit 118 shown in FIG. 10, for example (as one example, such component elements may be realized by separate processing circuits).

In addition, as described earlier, one or two or more component elements out of the examination state determining unit 114, the notification control unit 116, and the recording control unit 118 shown in FIG. 10 may be omitted from the ultrasonography apparatus according to the present embodiment. Even when one or two or more component elements out of the examination state determining unit 114, the notification control unit 116, and the recording control unit 118 shown in FIG. 10 is/are omitted, the ultrasonography apparatus according to the present embodiment is capable of taking the lead role in the processing (frequency setting process) in (1) described above and the processing (sound wave generation control process) in (2) described above relating to the ultrasonography method according to the present embodiment. Accordingly, even when one or two or more component elements out of the examination state determining unit 114, the notification control unit 116, and the recording control unit 118 is/are omitted, the ultrasonography apparatus according to the present embodiment is still capable of enabling the examiner to carry out an ultrasonographic examination using sound waves of a suitable frequency for the subject.

As described above, the ultrasonography apparatus according to the present embodiment carries out the processing (frequency setting process) in (1) described above and the processing (sound wave generation control process) in (2) described above for example as processing relating to the ultrasonography method according to the present embodiment. Here, the ultrasonography apparatus according to the present embodiment sets a suitable frequency for the subject in the processing (frequency setting process) in (1) described above and causes the probe to generate sound waves of the set frequency in the processing (sound wave generation control process) in (2) described above.

Accordingly, the ultrasonography apparatus according to the present embodiment is capable of enabling the examiner to carry out an ultrasonographic examination using sound waves of a suitable frequency for the subject.

The ultrasonography apparatus according to the present embodiment is capable of carrying out the processing shown in the first to fifth examples described above, for example, by further carrying out one or two or more processes out of the examination state determination process, the notification control process, and the recording control process described earlier, for example. Accordingly, by carrying out the processing shown in the first to fifth examples described earlier, the ultrasonography apparatus according to the present embodiment is capable of achieving the effects corresponding to the processing shown in the first to fifth examples described earlier.

The ultrasonography apparatus according to the present embodiment is capable of achieving the effects (A) and (B) given below, for example.

(A) In an ultrasonographic examination or an ultrasonographic diagnosis, individual differences between subjects, differences between types of organ and differences in skill between examiners (doctors, technicians, and the like) can be absorbed. Accordingly, the ultrasonography apparatus according to the present embodiment is capable of acquiring a favorable examination image (diagnostic image) for a plurality of organs (examples of examined parts) with a single apparatus without being dependent on differences in sex, age, the degree of obesity, and the disease condition between individuals.

(B) According to the processing relating to the fourth example described above, it is possible to give guidance on the position and/or inclination of the probe at which a normal examination result is obtained. That is, the ultrasonography apparatus according to the present embodiment can be said to be capable of simulating an examiner with high technical skills. Accordingly, by using the ultrasonography apparatus according to the present embodiment, even when an ultrasonographic examination is carried out by an examiner with little examination skill (for example, an inexperienced examiner), it is possible to acquire an examination image (diagnostic image) with higher clarity.

Although the present embodiment of the disclosure has been described by way of an ultrasonography apparatus as an example, the present embodiment is not limited to such. The present embodiment can be applied to a variety of appliances that are capable of carrying out the processing relating to the ultrasonography method according to the present embodiment, such as a medical appliance or a computer such as a PC (Personal Computer) or a server. The present embodiment can also be applied to a processing IC (Integrated Circuit) capable of being embedded in an appliance such as those described above, for example.

Program According to the Present Embodiment

When executed by a computer, a program for causing a computer to function as the ultrasonography apparatus according to the present embodiment (for example, a program capable of executing the processing relating to the ultrasonography method according to the present embodiment, such as the processing (frequency setting process) in (1) described above and the processing (sound wave generation control process) in (2) described above) is capable of enabling an examiner to carry out an ultrasonographic examination using sound waves of a suitable frequency for the subject.

Although a preferred embodiment of the present disclosure has been described above with reference to the attached drawings, the technical scope of the present disclosure is not limited to such embodiment. It should be understood by those skilled in the art that various modifications, combinations, sub-combinations and alterations may occur depending on design requirements and other factors insofar as they are within the scope of the appended claims or the equivalents thereof.

For example, although the provision of a program (computer program) for causing a computer to function as the ultrasonography apparatus according to the present embodiment has been described above, the present embodiment is also capable of providing a recording medium on which the program described above is stored.

The configuration described earlier is one example of an embodiment according to the present disclosure and naturally belongs to the technical scope of the present disclosure.

Additionally, the present technology may also be configured as below.

(1) An ultrasonographic system, comprising: an electronic memory to store a table relating subject information to a plurality of frequencies; and a frequency setting unit to set, as an examination frequency, one of the plurality of frequencies based on selection of subject information from the table, the examination frequency being used to perform an ultrasound examination on a subject corresponding to the selected subject information.

(2) The ultrasonographic system of (1), wherein the subject information includes information on race, gender and body type of the subject.

(3) The ultrasonographic system of (1) to (2), wherein the subject information further includes information on a body part to be examined by the ultrasound examination.

(4) The ultrasonographic system of (1) to (3), wherein the subject information includes disease information and subject condition.

(5) The ultrasonographic system of (1) to (4), further comprising: a sound wave generating unit to generate sound waves corresponding to the examination frequency set by the frequency setting unit, wherein the examination frequency is adjusted based an examination state.

(6) The ultrasonographic system of (1) to (5), further comprising: an examination unit to determine the examination state based on an examination image.

(7) The ultrasonographic system of (6), wherein the frequency setting unit specifies a range of frequencies based on the selected subject information, and the examination frequency is adjusted to a frequency within the range of frequencies based on the examination state.

(8) The ultrasonographic system of (6) to (7), further comprising: a notification unit to provide a notification based on the examination state.

(9) The ultrasonographic system of (6) to (8), wherein examination information is recorded in a storage medium as reference examination information based on the examination state.

(10) The ultrasonographic system of (9), wherein the examination information includes an examination probe position and an examination probe inclination.

(11) The ultrasonographic system of (6) to (10), wherein the examination state is determined based on a comparison of a clarity of the examination image with a predetermined threshold.

(12) The ultrasonographic system of (6) to (11), wherein the examination state is indicated as normal when the clarity of the examination image is above the predetermined threshold, and the examination state is indicated as not normal when the clarity of the examination image is equal to or below the predetermined threshold.

(13) The ultrasonographic system of (6) to (12), wherein examination information is recorded in a storage medium as reference examination information when on the examination state is normal.

(14) The ultrasonographic system of (9) to (13), further comprising: a notification unit to provide a notification based on the examination state or a notification based on the reference examination information.

(15) The ultrasonographic system of (14), wherein the notification based on the reference examination information includes at least one of an examination probe position and an examination probe inclination.

(16) The ultrasonographic system of (1) to (15), wherein the selected subject information is selected based on user operation.

(17) The ultrasonographic system of (1) to (15), wherein the selected subject information is selected based on communication with an external device.

(18) An ultrasonographic imaging method, comprising: storing a table relating subject information to a plurality of frequencies in an electronic memory; and setting, as an examination frequency, one of the plurality one of the plurality of frequencies based on selection of subject information from the table, the examination frequency being used to perform an ultrasound examination on a subject corresponding to the selected subject information.

(19) A non-transitory computer-readable medium storing computer-readable instructions thereon, the computer-readable instructions when executed by a computer cause the computer to perform an ultrasonographic imaging method comprising: storing a table relating subject information to a plurality of frequencies; and setting, as an examination frequency, one of the plurality one of the plurality of frequencies based on selection of subject information from the table, the examination frequency being used to perform an ultrasound examination on a subject corresponding to the selected subject information.

(20) An ultrasonography apparatus including:
a frequency setting unit setting a suitable frequency for a subject based on subject information showing the subject; and
a sound wave generation control unit causing a probe, which is capable of generating sound waves, to generate sound waves of the set frequency.

(21) The ultrasonography apparatus according to (10), wherein the subject information includes one or two or more pieces of information classifying the subject, information showing an examined part, information showing a disease content of the subject, and an information showing a condition of the subject.

(22) The ultrasonography apparatus according to (20) or (21), further including,
an examination state determining unit determining an examination state based on clarity of an examination image that is an image showing echoes produced from the subject as a result of the generated sound waves striking the subject, wherein the frequency setting unit adjusts the set frequency based on a determination result for the examination state.

(23) The ultrasonography apparatus according to (20) or (21), further including,
an examination state determining unit determining an examination state based on clarity of an examination image that is an image showing echoes produced from the subject as a result of the generated sound waves striking the subject, wherein the frequency setting unit specifies a suitable range of frequencies for the subject based on the subject information, shifts the set frequency in the specified range of frequencies, and sets the suitable frequency for the subject out of the shifted frequencies based on a determination result for the examination state.

(24) The ultrasonography apparatus according to (20) or (21), further comprising:
an examination state determining unit determining an examination state based on clarity of an examination image that is an image showing echoes produced from the subject as a result of the generated sound waves striking the subject; and
a notification control unit causing notification to be given, based on a determination result for the examination state.

(25) The ultrasonography apparatus according to (20) or (21), further including:
an examination state determining unit determining an examination state based on clarity of an examination image that is an image showing echoes produced from the subject as a result of the generated sound waves striking the subject; and
a recording control unit having reference examination state information showing a state where a normal examination is being carried out selectively recorded, based on a determination result for the examination state.

(26)

The ultrasonography apparatus according to (25), further including, a notification control unit operable when the determination result for the examination state does not indicate a state where a normal examination is being carried out, to cause notification to be given based on the reference examination state information and examination state information showing the examination state.

(27)

The ultrasonography apparatus according to any one of (22) to (26), wherein the examination state determination unit subjects the examination image to suitable image processing for the subject or for an examined part of the subject and determines the examination state based on the examination image after the image processing.

(28)

The ultrasonography apparatus according to any one of (20) to (27), further including the probe.

(29)

A ultrasonography method including:

setting a suitable frequency for a subject based on subject information showing the subject; and causing a probe, which is capable of generating sound waves, to generate sound waves of the set frequency.

(30)

A program causing a computer to execute:

setting a suitable frequency for a subject based on subject information showing the subject; and causing a probe, which is capable of generating sound waves, to generate sound waves of the set frequency.

REFERENCE SIGNS LIST

100 Ultrasonography apparatus
102 Control unit
104 Notification unit
110 Frequency setting unit
112 Sound wave generation control unit
114 Examination state determining unit
116 Notification control unit
118 Recording control unit
200 Probe

The invention claimed is:

1. An ultrasonographic system, comprising:
a probe configured to generate sound waves to examine a subject; and
circuitry configured to:
receive an input that corresponds to selection of first information related to the subject;
determine a first frequency based on the received input;
control the probe to generate at least a first sound wave at the first frequency;
obtain, based on the at least first sound wave, a first examination image of the subject;
determine at least one attribute of the first examination image;
determine a second frequency based on the at least one attribute;
control the probe to generate at least a second sound wave at the second frequency; and
obtain, based on the at least second sound wave, a second examination image of the subject.

2. The ultrasonographic system according to claim 1, wherein the first information includes second information on at least one of race, gender or body type of the subject.

3. The ultrasonographic system according to claim 1, wherein the first information includes second information on a body part of the subject.

4. The ultrasonographic system according to claim 3, wherein the first information further includes disease information and third information related to a condition of the subject.

5. The ultrasonographic system according to claim 1, wherein the circuitry is further configured to:
determine an examination state based on the at least one attribute; and
determine the second frequency based on the examination state.

6. The ultrasonographic system according to claim 5, wherein the circuitry is further configured to determine the examination state based on the second examination image.

7. The ultrasonographic system according to claim 5, wherein the circuitry is further configured to determine the second frequency within a range of frequencies, wherein the range of frequencies is based on the first information.

8. The ultrasonographic system according to claim 5, wherein the circuitry is further configured to provide a notification based on the examination state.

9. The ultrasonographic system according to claim 5, wherein the circuitry is further configured to record third information related to the examination state.

10. The ultrasonographic system according to claim 9, wherein the third information includes at least position information of the probe or inclination information of the probe.

11. The ultrasonographic system according to claim 9, wherein the circuitry is further configured to record the third information based on the examination state that is normal.

12. The ultrasonographic system according to claim 9, wherein the circuitry is further configured to provide a notification based on the third information.

13. The ultrasonographic system according to claim 12, wherein the notification includes at least one of position information of the probe or inclination information of the probe.

14. The ultrasonographic system according to claim 1,
wherein the at least one attribute corresponds to a measure of clarity of the first examination image, and
wherein the circuitry is further configured to determine the second frequency based on a comparison of the measure of clarity of the first examination image with a threshold.

15. The ultrasonographic system according to claim 14, wherein the circuitry is further configured to one of:
indicate an examination state as normal based on the measure of clarity of the first examination image that is greater than the threshold; or
indicate the examination state as abnormal based on the measure of clarity of the first examination image that is less than or equal to the threshold.

16. The ultrasonographic system according to claim 1, wherein the circuitry is further configured to select the first information based on a user operation.

17. The ultrasonographic system according to claim 1, wherein the circuitry is further configured to select the first information based on communication with an external device.

18. The ultrasonographic system according to claim 1, wherein the circuitry is further configured to determine the second frequency from a range of frequencies based on the first information.

19. An ultrasonographic imaging method, comprising:
receiving an input that corresponds to selection of first information related to a subject to be examined;
determining a first frequency based on the received input;
generating at least a first sound wave at the first frequency;
obtaining, based on the at least first sound wave, a first examination image of the subject;
determining at least one attribute of the first examination image;
determining a second frequency based on the at least one attribute;
generating at least a second sound wave at the second frequency; and
obtaining, based on the at least second sound wave, a second examination image of the subject.

20. A non-transitory computer-readable medium having stored thereon, computer-executable instructions for causing an ultrasonographic apparatus to execute operations, the operations comprising:
receiving an input that corresponds to a selection of first information related to a subject to be examined;
determining a first frequency based on the received input;
generating at least a first sound wave at the first frequency;
obtaining, based on the at least first sound wave, a first examination image of the subject;
determining at least one attribute of the first examination image;
determining a second frequency based on the at least one attribute;
generating at least a second sound wave at the second frequency; and
obtaining, based on the at least second sound wave, a second examination image of the subject.

* * * * *